United States Patent [19]

Turner et al.

[11] Patent Number: 5,624,537
[45] Date of Patent: Apr. 29, 1997

[54] BIOSENSOR AND INTERFACE MEMBRANE

[75] Inventors: Robin F. B. Turner; Douglas G. Kilburn, both of Vancouver; Michael R. Phelps, Kingston, all of Canada

[73] Assignee: The University of British Columbia - University-Industry Liaison Office, Vancouver, Canada

[21] Appl. No.: 309,338

[22] Filed: Sep. 20, 1994

[51] Int. Cl.$^6$ .................................................. G01N 27/26
[52] U.S. Cl. .......................... 204/403; 204/415; 204/418; 205/778; 435/287.1; 435/817; 435/287.9
[58] Field of Search ............................. 204/403, 418, 204/153.12, 415; 435/817, 288, 291

[56] References Cited

U.S. PATENT DOCUMENTS

| 5,165,407 | 11/1992 | Wilson et al. | 204/415 |
| 5,254,223 | 10/1993 | Josowicz et al. | 204/59 R |
| 5,326,449 | 7/1994 | Cunningham | 204/415 |

OTHER PUBLICATIONS

Koopal, C.G.J. and Nolte, R.J.M., "Highly stable first-generation biosensor for glucose utilizing latex particles as the enzyme–immobilizing matrix," *Enzyme and Microbial Technology*, 16(5):402–408 (1994). No month available.

Soldatkin, A.P. et al., "Glucose sensitive conductometric biosensor with additional Nafion membrane: reduction on influence of buffer capacity on the sensor response and extension of its dynamic range," *Analytica Chimica Acta*, 288(3):197–203 (1994). No month available.

Vaidya, R. and Wilkins, E., "Application of Polytetrafluoroethylene (PTFE) Membranes to Control Interference Effects in a Glucose Biosensor," *Biomedical Instrumentation & Technology*, 27(6):486–494 (1993). No month available.

Rishpon, J. et al., "Amperometric Glucose Sensors Based on Glucose Oxidase Immobilized in Nafion," *Electroanalysis*, 6(1):17–21 (1994). No month available.

Wang, J. and Wu, H., "Permselective lipid–poly(o-phenylenediamine) coatings for amperometric biosensing of glucose," *Analytica Chimica Acta*, 283(2):683–688 (1993). No month available.

Uhegbu, C.E. et al., "Initial Studies of a New Approach to the Design and Use of Enzyme–Based Reactor/Sensor Systems: Amperometric System for Glucose," *Analytical Chemistry*, 65(18):2443–2451 (1993). No month available.

Rohde, E. et al., "Development of a flow–through electrochemical detector for glucose based on a glucose oxidase–modified microelectrode incorporating redox and conducting polymer materials," *Analytica Chimica Acta*, 278(1):5–16 (1993). No month available.

Koshy, A. et al., "Elimination of electrochemically–active interferents in amperometric biosensor measurements; application to on–line monitoring of glucose and glutamate," *Analytical Letters*, 26(5):831–849 (1993). No month available.

(List continued on next page.)

*Primary Examiner*—Bruce F. Bell
*Attorney, Agent, or Firm*—Christensen O'Connor Johnson & Kindness PLLC

[57] ABSTRACT

A regenerable biosensor probe adapted for positioning in a bioreactor comprises a selectively permeable interface membrane, a porous protein-receiving matrix adjacent to the interface membrane, an indicating electrode, an inlet conduit through which fresh protein conjugate may flow to the protein-receiving matrix, and an outlet conduit through which spent protein conjugate may be removed from the protein-receiving matrix. A selectively permeable interface membrane, which may be used in a biosensor system to separate biochemical, optical or other processes from an analyte matrix comprises a supporting mesh, a perfluorosulfonic acid polymer impregnated substrate and a homogenous film of perfluorosulfonic acid polymer.

A method of preparing this interface membrane comprises fixing a substrate on to a supporting mesh to form a substrate membrane, casting a perfluorosulfonic and polymer on the substrate membrane and curing the product to so formed.

12 Claims, 12 Drawing Sheets

OTHER PUBLICATIONS

Bradley, J. and Schmid, R.D., "Optimisation of a biosensor for *in situ* fermentation monitoring of glucose and concentration," *Biosensors and Bioelectronics*, 6:669–674 (1991). No month available.

Brooks, S.L. et al., "Development of an On–line Glucose Sensor for Fermentation Monitoring," *Biosensors*, 3:45–56 (1987–88). No month available.

Cleland, N. and Enfors, S.–O., "Monitoring glucose consumption in an *Escherida coli* cultivation with an enzyme electrode," *Anal. Chim. Acta*, 163:281–285 (1984). No month available.

Cleland, N. and Enfors, S.–O., "Control of Glucose–Fed Batch Cultivations of *E. coli* by Means of an Oxygen Stabilized Enzyme Electrode," *Eur. J. Appl. Microbio. Biotechnol.*, 18:141–147 (1983). No month available.

de Alwis, U. and Wilson, G.S., "Strategies for the reversible immobilization of enzymes by use of biotin–bound anti–enzyme antibodies," *Talanta*, 36(1/2):249–253 (1989). No month available.

Enfors, S.–O., "Oxygen stabilized enzyme electrode for D–glucose analysis in fermentation broths," *Enzyme Microbiol. Technol.*, 3:29 (1981). No month available.

Foulds, N.C. and Lowe, C.R., "Enzyme Entrapment in Electrically Conducting Polymers," *J. Chem. Soc., Faraday Trans., I.*, 82:1259–1264 (1986). No month available.

Harrison, D.J. et al., "Characterization of Perfluorosulfonic–Acid Polymer Coated Enzyme Electrodes and a Miniaturized Integrated Potentiostat for Glucose Analysis in Whole Blood," *Anal. Chem.*, 60:2002–2007 (1988). No month available.

Lee, J.–S. et al., "A new glucose sensor using microporous enzyme membrane," *Sensors and Actuators B.*, 3:215–219 (1991). No month available.

Phelps, M.R. et al., "Technology for Regenerable Biosensor Probes Based on Enzyme–Cellulose Binding Domain Conjugates," *Biotechnol. Prog.*, 10:433–440 (1994). No month available.

Renneberg, R. et al., "Enzyme sensor–FIA system for on–line monitoring of glucose, lactate and glutamine in animal cell cultures," *J. Biotech.*, 21:173–186 (1991). No month available.

Wang, J., "Permselective Coatings for Amperometric Biosensing," In *Biosensors and chemical sensors: optimizing performance through polymeric materials*, Eddman, P.G. and Wang, J., Eds., Symposium series 487:125–132 (ACS: New Mexico State University, 1992). No month available.

BIOSENSOR AND INTERFACE MEMBRANE

FIELD OF THE INVENTION

This invention generally relates to biosensors and, more particularly, to interface membrane systems which may be used with biosensors.

BACKGROUND OF THE INVENTION

Since the enzyme electrode was first conceived, a significant interest has developed in the field of biosensors because of the simplicity and selectivity of these sensors. This increase in interest began in the 1980's, as evidenced by the publication of a new international journal *Biosensors*[1]. The rapid growth of biotechnology in the last decade has now created a demand for more and better on-line sensors that can be interfaced with computers to control and optimize bioprocesses. Numerous enzyme electrode configurations have been published, although the amount of research activity today is too great to be covered in a single review[2]. Present-day applications of biosensors can be found in industrial bioprocess monitoring, environmental monitoring, the food and drink industry, and clinical and *in vivo* application in medicine[3,4].

[1] Stoecker, P. W.; Yacynyeh, A. M. Chemically Modified Electrodes as Biosensors. *Sel. Elec. Rev.* 1990, 12, 137–160.

[2] Preitag, R. Applied Biosensors. *Curr. Opin. Biotech.; Anal. Biotech.* 1993, 4, 75–79.

[3] Schultz, J. S. Sophisticated Descendants of The Canary in The Coal Mine Are Based on Molecular Components of Plants and Animals Bound to Microscope Electrodes or Optical Fibers. *Scientific American* 1991, 264, 64–69.

[4] Reach, G.; Wilson, G. S. Can Continuous Glucose Monitoring be Used For the Treatment of Diabetes! *Anal. Chem.* 1992, 64, 381–386.

The increasing commercial importance of bioreactors has stimulated research in the area of on-line monitoring of microbial and animal cell bioreactors in order to optimize performance conditions. The specificity and selectivity provided by the biological component of biosensors offer enormous potential, in principle, for continuous, on-line analysis in complex media. Despite the number of biosensor research papers published each year in the scientific literature, relatively few bioprocess sensors are commercially available. Unfortunately, many practical problems remain which have prevented the widespread application of on-line biosensors under real conditions and these have not been successfully addressed by researchers to data. In particular, the development and commercialization of biosensors has been slowed by problems of instability such as drift of the sensor signals, narrow measuring ranges for the analyte and long response time.

Short term instabilities typically result from changes in the enzyme component, such as inhibition or deactivation by components of the analyte medium. Long term instabilities (drive of the sensors signal over time) may be due to time-dependent changes in the sensor calibration constants which are caused by membrane fouling or electrode poisoning. Perm-selective membranes for amperometric biosensing have been investigated as a means to address these problems. A literature review of these membranes is provided in Wang, 1992[5].

[5] Wan, J. Permselective Coatings For Amperometric Biosensing. In *Biosensors and Chemical Sensors: Optimizing Performance Through Polymeric Materials*; Eddman, P. G., Wang, J., Eds.; ACS: New Mexico State University, 1992; Symposium Series 487, pp 125–132.

Although the lifetime of an enzyme in a reaction system may be prolonged in some cases, the denaturization of enzymes may be irreversible and replacement of the enzyme when the activity has degraded to an unsatisfactory degree may eventually be necessary with virtually all of the commercially available biosensors (whether on-line or not). The capability to replace only the enzyme component of the sensor without disrupting the process would not only extend the sensor operating lifetime but would allow for a substitution of other enzymes in order to change the analyte specificity of the sensor.

A few sensor systems have been described in the literature with the capacity for enzyme replacement. Brooks et al (1987/88)[6] and Bradley and Schmid (1991)[7] have described the immobilization of enzyme on graphite discs which could be replaced manually. There is no contemplation of in situ, automatic exchange of the enzyme, that is, without dismantling the sensor or interrupting the fermentation. Pieters and Bardeletti (1992)[8] described the immobilization of enzymes to magnetic beads which can then be manipulated using magnetic fields. This technique has been used in waste-water treatment, affinity separation processes, cell sorting, immunoassays and drug delivery. Specifically, glucose oxidase has been reversibly immobilized in an enzyme reactor coupled to a flow injection analysis system using a chain of biospecific reactions based on the binding of biotin-labelled (ie. biotinylated) antibodies to an avidin coated matrix (de Alwis and Wilson 1989[9]).

[6] Brooks, S. L.; Ashby, R. E.; Turner, A. P. F.; Calder, M. R.; Clarke, D. J. Development of an On-Line Glucose Sensor For Fermentation Monitoring, *Biosensors* 1987/88, 3, 45–56.

[7] Bradley, J.; Schmid, R. D. Optimization of a Biosensor For In situ Fermentation Monitoring of Glucose Concentration. *Biosensor & Bioelectronics* 1991, 6, 669–674.

[8] Pieters, B. R.; Bardeletti, G. Enzyme Immobilization on a Low-Cost Magnetic Support: Kinetic Studies on Immobilized And Coimmobilized Glucose Oxidase And Glucoamylase. *Enzyme Microb. Technol.* 1992, 14, 361–370.

[9] de Alwiss, U; Wilson, G. S. Strategies For The Reversible Immobilization of Enzymes by Use of Biotin-Bound Anti-Enzyme Antibodies, *Talanta* 1989, 36, 249–253.

In summary, at the present time, only a few reaction parameters can be reliably monitored on-line (eg. temperature, pH, dissolved oxygen tension, stir rate) without the use of highly sophisticated and costly instrumentation. The analysis of fermentation substrates, products and metabolites is usually achieved by off-line methods[10]. However, optimal control of a bioprocess today requires that measurable parameters be determined as frequently as possible, which in turn requires frequent sampling that increases the risk of contamination. Furthermore, off-line methods are usually to slow to be used in a closed-loop control system, that it is often difficult to ensure that samples are not significantly degraded or changed during the sampling-analysis procedure. A sensor system based on an in situ probe which could provide continuous, real-time analysis would be extremely valuable, particularly for high-density, fed-batch processes. The advantages and disadvantages of automated sampling systems in contrast with in situ probes have been discussed in the literature (Ogbomo et al, 1990[11]; Bradley et al, 1991[12]; Filippini et al, 1991[13]). The practical concerns involved in using an in situ biosensor probe, such as in situ sterilizability, long-term stability, adequate measuring range, and membrane fouling, have thus far prevented the widespread application and commercialization of this approach. Attempts to address these problems have heretofore been largely unsuccessful (Enfors and Molin, 1978[14]; Cleland and Enfors, 1983[15]; Bradley et al., 1988[16], 1991[17] and Brooks et al., 1987/88[18]; Buhler and Ingold, 1976[19]). In each of these probe designs, the combined functions of enzyme replacement and recalibration of the sensor cannot be performed without operator intervention. Thus, an operator must be standing by during a long fermentation run to manually replace the enzyme component periodically and then recalibrate the sensor.

[10] Supra at 6.

[11] Ogbomo, I.; Prinzing, U.; Schmidt, H. L. Prerequisites For The Control of Microbial Processes by Flow Injection Analysis. *J. Biotechnol.* 1990, 14(1), 63–70.

[12] Bradley, J.; Stöckleim, W.; Schmid, R. D. Biochemistry Based Analysis Systems for Bioprocess Monitoring and Control. *Process Contr. Qual.* 1991, 1, 157–183.

[13] Filippini, C.; Sonnleitner, B.; Fiechter. A., Bradley, J.; Schmid, R. On-Line Determination of Glucose in Biotechnological Processes: Comparison Between FLA And an In situ Enzyme Electrode. *J. Biotechnol.* 1991, 18, 153–160.

[14] Enfors, S. O.; Nilsson, H. Design And Response Characteristics of an Enzyme Electrode For Measurement of Penicillin in Fermentation Broth. *Enzyme Microbiol. Technol.* 1979, 1, 260–264.

[15] Cleland, H., Enfors, S. O. Monitoring Glucose Consumption in an *Escherichia coli* Cultivation With an Enzyme Electrode. *Anal. Chim. Acta.* 1984b, 163, 281–285.

[16] Bradley, J.; Anderson, P. A.; Dear, A. M.; Ashby, R. E.; Turner, A. P. F. Glucose Biosensors for the Study and Control of Baker's Compressed Yeast Production. In *Computer Applications in Fermentation Technology: Modelling and Control of Biotechnological Processes;* Fish, N. M., Fox, R. I., Thornhill, N. F., Eds.; Elsevier Applied Science: New York, 1988; pp 47–51.

[17] Supra at 7.

[18] Supra at 6.

[19] Bühler, H., Ingold, W. Measuring pH and Oxygen in Fermenters. *Process Biochem.* 1976, 11(3), 19–24.

The outer membrane of a biosensor is very important, as it represents the interface between the sensor and the analyte medium. The purpose of this interface membrane is to allow the diffusion of analytes and (in electrochemical reaction) electrolytes into the investigative or analysts layer while excluding potential interfering species which may be present in the analyte medium, such as cells, proteins, inhibitors or interferents.

In U.S. Pat. No. 5,165,407 to Wilson et al., an implantable glucose sensor is provided having an enzyme immobilized on an indicating electrode and a permeable polyurethane membrane applied over the sensor body to prevent fouling of the electrode and denaturization of the enzyme. This membrane, as with others currently employed, is integrated with the sensor system and can not be replaced or reused with other systems.

The objects of this invention are to obviate or mitigate the disadvantages of the current in situ biosensor probes and the disadvantages of current membrane systems for use generally with biosensor probes.

SUMMARY OF THE INVENTION

In a first aspect of the present invention a regenerable biosensor probe, adapted for operation in an environment characterized by the presence of biological molecules which are substrates for or products produced by enzymes or cells in order to determine the presence of said molecules is provided which comprises a selectively permeable interface membrane which separates the biochemical and optical or electrochemical processes form the analyte matrix environment when the probe is in place; an protein-receiving matrix adjacent to the interface membrane; an indicating electrode covered with an electrically insulative material said electrode abutting, at one of its ends, the protein-receiving matrix; an inlet conduit through which fresh protein-conjugate may flow to the protein-receiving matrix; and an outlet conduit through which spent protein-conjugate may be removed from the protein-receiving matrix. This biosensor probe is capable of functioning in a closed-loop or computer-controlled system.

In a second aspect of the present invention a selectively permeable interface membrane is provided which may be used with any type of biosensors to separate the biochemical and optical or electrochemical processes from the analyte matrix which comprises a supporting mesh, a perfluorosulfonic acid-impregnated substrate and a homogeneous film of perfluorosulfonic acid polymer.

In a third aspect of the present invention a method of preparing a selectively permeable interface membrane is provided which method comprises fixing a substrate onto a supporting mesh to form a substrate membrane, casting a perfluorosulfonic acid polymer film on the substrate membrane and curing the product so formed.

In a preferred form of the first aspect of the present invention, the protein of interest is immobilized by a conjugation with the cellulose binding domain (CBD) of cellulases from bacteria of the genus Cellulomonas. These cellulases have a modular structure consisting of two or more structurally separate domains. The binding domain functions independently of the catalytic domain and can be chemically or genetically conjugated to other proteins (eg. enzymes) which then bind strongly to cellulose. Accordingly, the porous protein-receiving matrix of the biosensor disclosed herein preferably comprises cellulose. Under the appropriate solution conditions, the binding of the protein-CBD conjugate to the protein-receiving matrix in the biosensor comprising cellulose can be disrupted and the conjugate protein eluted from the cellulose matrix. The loading and eluting of the protein conjugate is described in greater detail hereinbelow. The exact nature of the binding mechanism has not been determined, however, the binding to cellulose has been reported to be virtually instantaneous. Previously published CBD binding studies indicate that adsorption of the CBD to cellulose was complete within the shortest incubation time feasible under the conditions of the experiments (ie., 0.2 minutes) (Gilkes et al, 1992[20]), but the actual adsorption kinetics are likely much faster.

[20] Gilkes, N. R.; Jervis, E.; Henrissat, B.; Tekant, B.; Miller, R. C. Jr.; Warren, R. A. J.; Kilburn D. G. The Adsorption of a Bacterial Cellulose And Its Two Isolated Domains to Crystalline Cellulose. *J. Biol. Chem.* 1992, 267(10), 6743–6749.

Researchers have previously used CBD for the immobilization of proteins and as an affinity tag for the purification of recombinant proteins using cellulose columns (Kilburn et al, 1992[21]). What has not been disclosed or heretofore examined is the use of the reversible binding properties of the CBD to proteins in a biosensor context, and in particular, to an in situ, regenerable biosensor, capable of functioning in either a closed-loop or open system, as contemplated in the present invention.

[21] Kilburn, D. G.; Turner, R. F. B.; Coutinho, J. B.; Din, N.; Gilkes, N. R.; Greenwood, J. M.; Hobbs, J. B.; Miller, R. C. Jr.; Ong, E.; Phelps, M. R.; Ramiz, C.; Warren, R. A. J. Cellulose Binding Domains: Applications in Biotechnology. *Proc. Cellucon 92*, In Press.

One of the key advantages of the use of a protein conjugate comprising CBD and a cellulose matrix within a biosensor is the ability to calibrate, measure and replace protein during sampling and analysis procedures in the biosensor in a simple, reliable way. The combination in the present invention of the use of a protein conjugate comprising CBD, the cellulose matrix in the biosensor and the capability of engaging this biosensor to hardware enabling the creation of an on-line system allows for efficient and reliable feedback control for the optimization of reaction conditions in fed-batch processes. One application of the biosensor of the present invention is the commercial production of recombinant proteins. The production of recombinant proteins can be optimized by maximizing the biomass yield on substrate to obtain a high cell density and then maximizing cell specific productivity through high rates of gene expression. High biomass yield on a given substrate can be obtained by controlling metabolism and minimizing the excretion of an inhibitory metabolites through the regulation of substrate levels (Smith and Bajpai, 1985[22]). Due to the importance of glucose as the main carbon and energy source for microbial growth in industrial fermentations, applying the biosensor technology of the present invention to glucose monitoring would be beneficial in order to operate the bioprocesses under optimum conditions.

[22] Smith, M.; Bajpai, R. Fed-Batch Control of *Escherichia coli* Fermentation to High Cell Density. *Proc. 15th Ann. Biochem. Eng. Symp.* 1985, 15, 34–44.

In general, a closed-loop control system utilizes information encoded in any number of distinct (either independent or related) signals derived from instrumentation that may operate either on-line (ie., within the controlled bioreactor environment) or off-line (ie., external to the bioreactor environment). The information is processed, either digitally or analog, according to some specified algorithm with the objective of making a decision regarding appropriate adjustments in some control variable(s) (eg., the rate of glucose infusion in a fed-batch fermentation using glucose as the main carbon source). The invention of this disclosure would provide an important input signal to such a control system. The availability, reliability and quality of this signal are the particular advantages of the invention.

A very simple, hypothetical closed-loop control system based on a single input from an on-line glucose sensor might be configured as follows: (1) the sensor is prepared and installed in the bioreactor comprising the biosensor of the present invention; (2) a particular protein concentration is determined/specified as a set-point concentration at which the control system is intended to maintain in the bioreactor throughout some specified interval of the fermentations; (3) in operation, the sensor signal is conveyed via a standard analog-to-digital converter (ADC) interface to a standard proportional-integral-derivative (PID) controller implemented in the software of a personal computer; (4) the output signal from the controller is applied via a standard interface bus (eg. RS-232) to a hardware actuator system that adjusts the rate of glucose infusion into the bioreactor fee port. The operating program running on the personal computer would be designed to accept auxiliary information regarding periodic off-line protein analyses; this information would be used to check and update the sensor calibration parameters also as described in the thesis by M. R. Phelps. If the sensor parameters stray beyond certain specified limits, the control system is interrupted (and placed temporarily in some safe stand-by mode) and the sensor is guided through a sequence of steps, using computer-controlled pumps and actuators, outlined in FIG. 2. This sequence of steps would take less than 10 minutes and would be required only rarely (perhaps not at all) during a fermentation. Recalibration could be carried out either by perfusing the sensor with glucose concentration standards or by utilizing the auxiliary information from a series of off-line analyses, obtained during an interval where the bioreactor glucose concentration is allowed to vary. This is a very simple example—and an overly simplified description—of a hypothetical system that could be modified in a variety of ways. It is not the intention of the present authors, however, to detail the closed-loop system any further.

The provision of an on-line system in accordance with the present invention allows optimal control (with respect to the analyte) of the bioprocess monitored by the biosensor and ensures that the biological molecule of interest is measured as frequently as required without the risk of contamination of the process. Currently used off-line methods are usually too slow to be used in a closed-loop (computer) control system, and it is often difficult to ensure that samples are not significantly degraded or changed during the sample/analysis procedure. The biosensor of the present invention using an in situ probe provides continuous, real-time analysis which is particularly useful for high-density, fed-batch processes. The on-line biosensor of the present invention allows the complete process of diagnosis, regeneration and recalibration to be performed in situ and with the capability of the processes being conducted under computer control. The applications of the biosensor are widespread given the possibility of conjugating CBD to other biological molecules, including varied proteins such that the sensor hardware can be used for monitoring a variety of different analytes. The biosensor of the present invention is in contrast to the probe designs heretofore known and available in which replacement and recalibration of the sensor cannot generally be performed without operator intervention.

The third aspect of the present invention which provides a selectively permeable interface membrane is very important, as it represents the interface between a biosensor and the analyte medium. The purpose of the interface membrane is to allow diffusion of the biological molecules of interest into the biosensor while excluding interfacing species which may be present in the analyte medium, such as cells, proteins, enzymes inhibitors or other interferents. The interface membrane also provides significant mass transfer resistance which increases the linearity of response and the working range of the sensor. The interface membrane of the present invention additionally provides an autoclavable aseptic barrier between the biosensor and the external environment.

The interface membrane of the present invention comprises a supporting mesh, a perfluorosulfonic acid polymer inpregnated substrate and a homogenous film of perfluorosulfonic acid polymer. The homogenous film comprises the outer-most layer of the membrane and forms, when the membrane is in place, a biocompatible interface between the biosensor and the reaction environment.

The use of perfluorosulfonic acid (tradename Nafion) polymer as part of a separate biomembrane system, formed in accordance with the present invention, has not heretofore been contemplated. Nafion has, however, been used in various ways in biosensor systems. In U.S. Pat. No. 5,082, 550 to Rishpon et al., perfluorosulfonic acid polymer was used as an enzyme matrix and coated on the biosensor electrode. It is not contemplated in this patent to prepare a detachable, unitary perfluorosulfonic acid polymer membrane in accordance with the present invention.

One of the key advantages of the interface membrane of the present invention is the fact that it may be used in conjunction with a wide variety of biosensors and bioreactors. Its use is not limited to the biosensor disclosed in the present invention.

In summary, all of the practical concerns of using an in situ biosensor probe, such as in situ sterilizability, long-term and short-term stability, adequate measuring range and membrane fouling which has thus far prevented the widespread application and commercialization of this approach, have been overcome by the regenerable biosensor probe of the present invention. In addition, and equally importantly, the selectively permeable interface membrane of the present invention provides:

(1) a permselective diffusion membrane that permits the analyte (and oxygen) to enter the sensor, while excluding potential interfering species that could foul the electrode of denature, or inhibit the activity of, the biological molecule of interest;

(2) an autoclavable, aseptic barrier that ensures bioprocess compatibility;

(3) an interfacial surface that is sufficiently biocompatible so that the membrane itself does not become fouled and experience a change in characteristics which would ultimately result in drift of the sensor calibration; and (4) a membrane which is separate and distinct from the other biosensor components.

BRIEF DESCRIPTION OF THE DRAWINGS

The accompanying drawings, which are incorporated in and form a part of the specification, illustrate embodiments of the present invention and, together with the description, serve to explain the principles of the invention. In the drawings.

DETAILED DESCRIPTION OF THE INVENTION

A. Regenerable Biosensor Probe

In accordance with the first aspect of the present invention, the basic design of the biosensor comprises an indicating electrode, a porous protein-receiving matrix and a protective interface membrane, all incorporated into a stainless steel probe for insertion into the bioreactor. Inlet and outlet conduits in the probe body allow for perfusion of the protein-receiving matrix with the protein conjugate solution and the elution buffer as described hereinbelow. The indicating electrode can be raised to permit complete perfusion of the protein-receiving matrix and then lowered into contact with this matrix to facilitate substrate monitoring. This is also described further hereinbelow.

In a preferred form, the protein-receiving matrix is a porous cellulose matrix. Further, it is preferred that the protein conjugate comprises the CBD of Cellulomonas most preferably, *C. fimi*.

Figure 1:
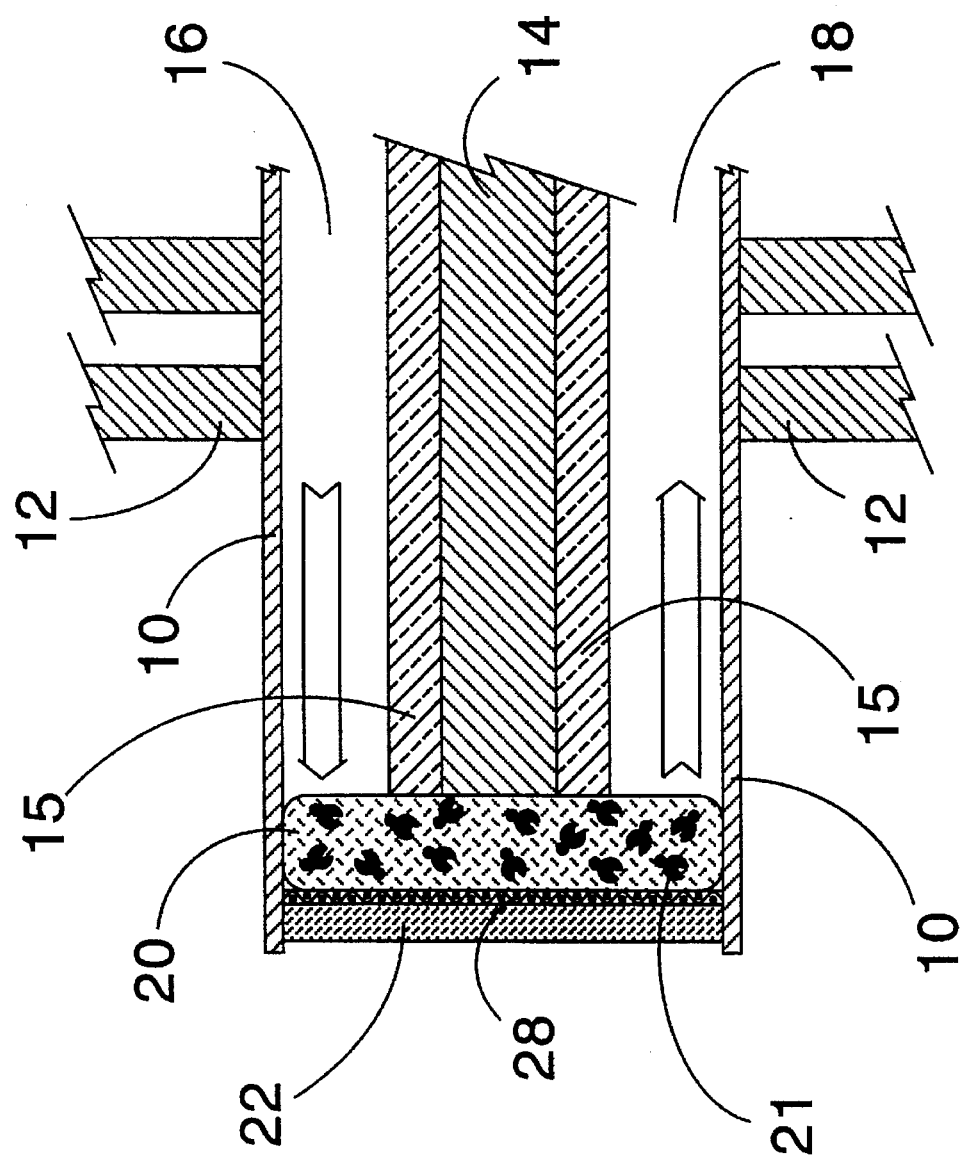
FIG. 1 is a schematic representation of a biosensor based on CBD-immobilized enzymes.

The components of the preferred form of biosensor in accordance with the present invention are illustrated schematically in FIG. 1.

FIG. 1 shows a biosensor probe 10 placed across wall 12 of a bioreactor. Biosensor probe 10 includes indicating electrode 14 (covered with insulating material 15), inlet conduit 16, outlet conduit 18 and a porous protein-receiving matrix 20 which abuts one end of electrode 14. A protein-CBD conjugate is indicated by numeral 21. An interface membrane is indicated generally at 22. The specifics of the interface membrane are shown in more detail in FIGS. 3 and 4.

Figure 3:
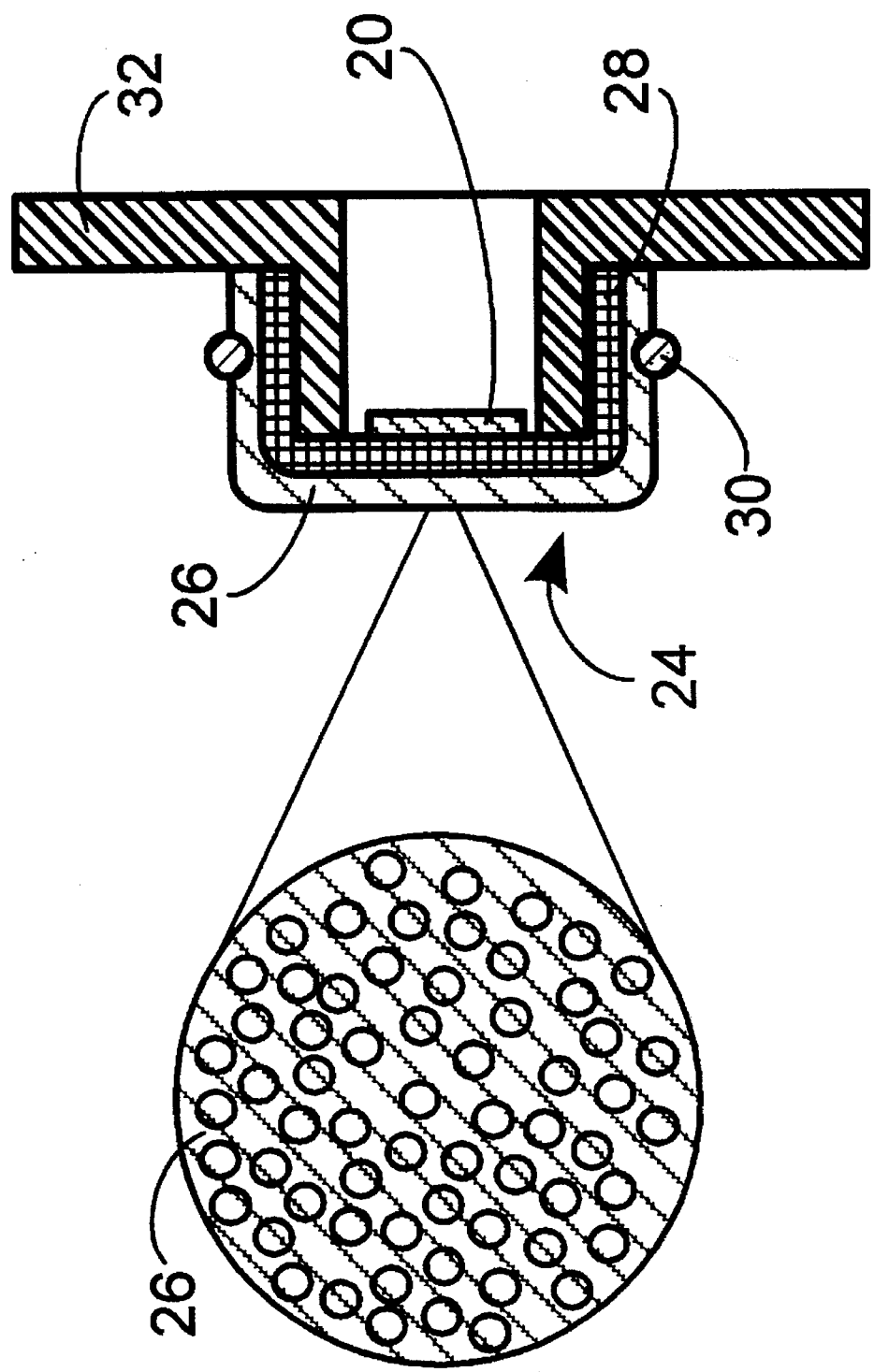
FIG. 3 is a schematic representation of a perfluorosulfonic acid polymer/cellulose triacetate interface membrane.
Figure 4:
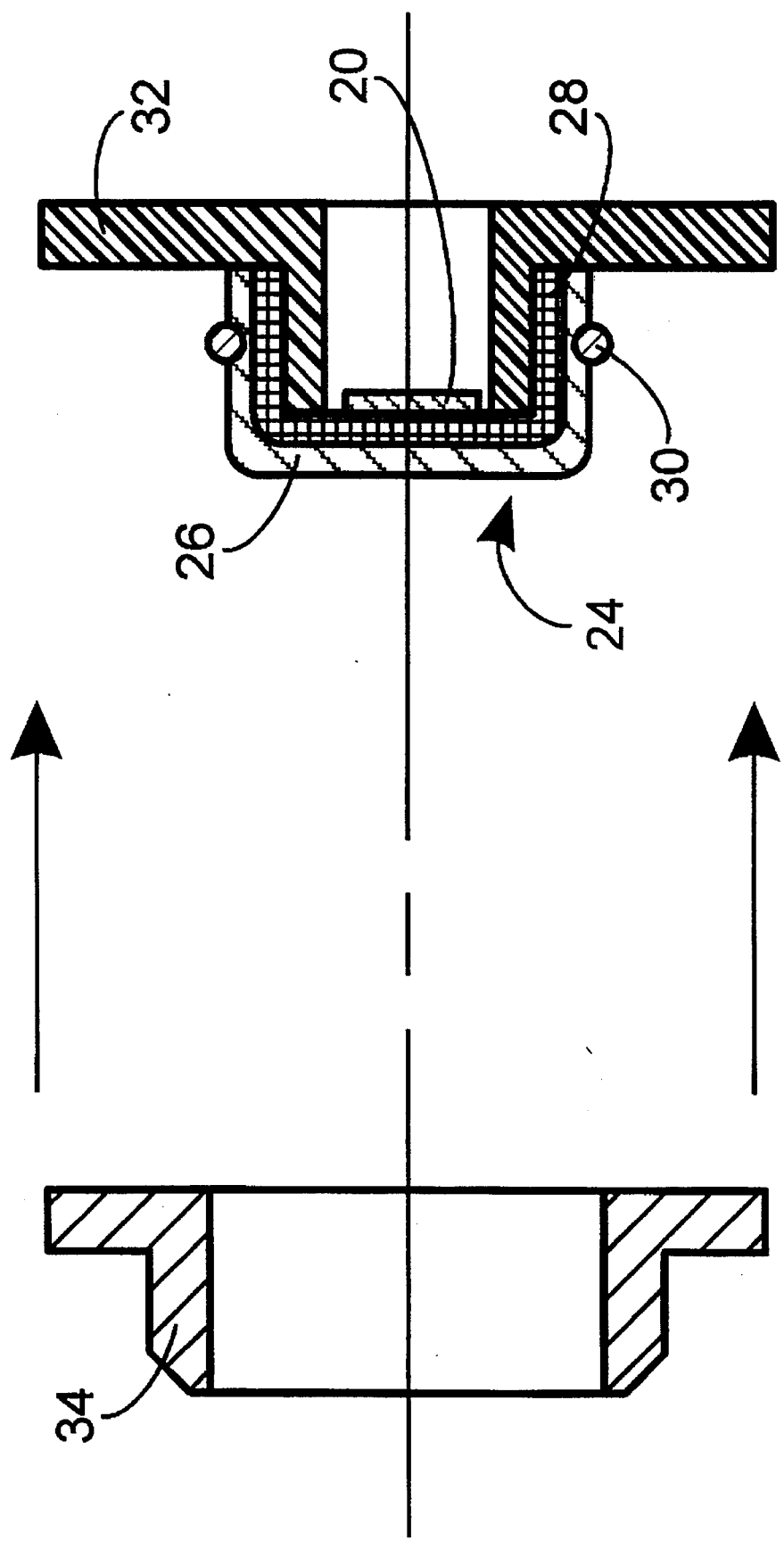
FIG. 4 is a schematic representation of the assembly of an interface membrane onto a biosensor probe.

With reference to FIGS. 3 and 4, there is depicted generally an interface membrane 24 assembly which is detachable from biosensor probe 10 (and is shown in this detached form). Interface membrane 24 comprises a perfluorosulfonic acid polymer-inpregnated substrate layer 26, supporting mesh 28 and retaining wire 30. In use, interface membrane 24 is disposed on membrane cartridge 32 and abuts protein-receiving matrix 20. Optionally, a retaining cap 34 may be used to secure interface membrane 24 in place on the tip of biosensor probe 10. FIG. 3 shows an exploded view of the perfluorosulfonic acid polymer (Nafion) layer 26. The cellulose matrix for immobilization of the protein-CBD conjugate is enclosed in a chamber formed by the probe body, the interface membrane and the indicating electrode unit. The indicating electrode, as discussed above, can be raised and lowered via a threaded shaft. When necessary, the indicating electrode unit is raised and the protein is eluted by perfusing the cellulose matrix with a suitable elution buffer (eg. distilled water, sodium hydroxide or guanidine hydrochloride), followed by perfusion with a soluble protein-CBD conjugate to replace the immobilized protein. In operation, the indicating electrode is lowered such that the cellulose matrix is sandwiched between the interface membrane and the indicating electrode. The protein-receiving matrix is filled with electrolyte which equilibrates with the electrolyte of the external analyte solution.

Figure 2:
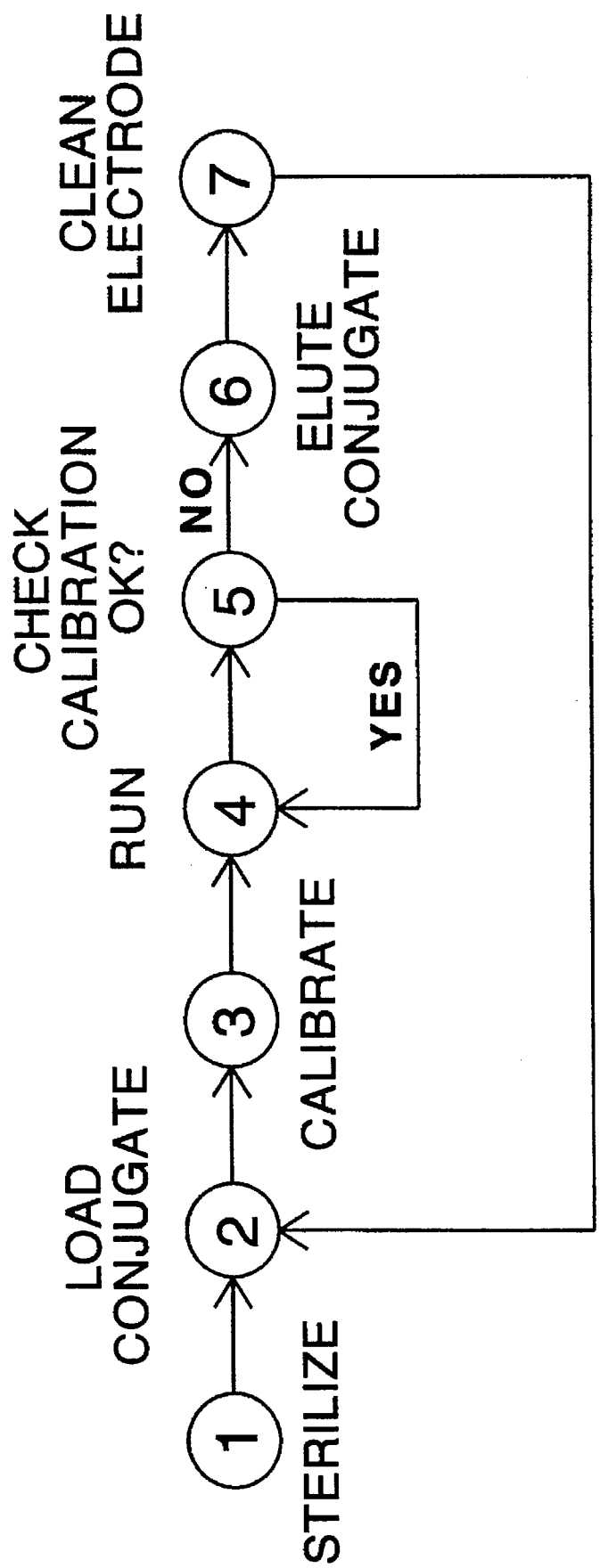
FIG. 2 is a process flow diagram demonstrating the principle of operation of a fermentation monitoring system using a regenerable biosensor probe.

FIG. 2 outlines the preferred principle of operation of the biosensor system for continuous fermentation monitoring. In one application of this invention, the protein to be conjugated to CBD is an enzyme. The entire probe, exclusive of the enzyme, is sterilized (indicated at Step 1) in situ during steam sterilization of the fermenter and contents. Following sterilization, the enzyme is loaded into the sensor by perfusion of the cellulose matrix with soluble enzyme-CBD conjugate, resulting in immobilization of the enzyme (behind the sterile barrier provided by the interface membrane) via attachment of the CBD. This loading is indicated at Step 2. The sensor is calibrated during the addition of the enzyme substrate to the fermenter. This calibration is indicated at Step 3. Periodically during the fermentation, as shown at Step 4, the sensor calibration can be checked at Step 5 by analysis of samples of the broth or, by pumping internal calibration standards through the enzyme chamber.

If the internal calibration check indicates that the biosensor performance is satisfactory, fermentation continues at Step 4. If performance has deteriorated to an unacceptable degree (Step 6) due to deactivation of the enzyme or electrode fouling, then the enzyme can be eluted (Step 4) by perfusion of the cellulose matrix with elution buffer. The biosensor is then reloaded (Step 2) with fresh enzyme-CBD conjugate as before, the sensor is recalibrated using the internal calibration standards and the fermentation monitoring continues. The sensor calibration can be verified, if desired, by comparison of the sensor/biosensor output with substrate analysis of a sample of the fermentation broth. Each of these steps of sampling, calibration and adjustment may be conducted using a closed-loop system.

The proteins of interest may be conjugated to CBD by any known genetic or chemical method. The methods disclosed in U.S. Pat. No. 5,340,731 to Kilburn et al. are incorporated herein by reference. In a preferred form of the present invention, the CBD is chemically conjugated to the enzyme using glutaraldehyde. It is to be clearly understood, that the present invention is not limited to a particular method of conjugation.

The operation of the biosensor of the present invention is based on the amperometric detection of hydrogen peroxide produced as a by-product of the enzymatic oxidation of a substrate by its enzyme catalyst. A potentiostat is used to maintain the necessary bias potential for the electrochemical oxidation of hydrogen peroxide at a noble metal indicating electrode and also converts the substrate-dependent electrode current into a usable output voltage. In a preferred form, the enzyme is conjugated to CBD, and the conjugate so formed is pumped into the porous protein-receiving matrix, which is preferably a cellulose matrix. The cellulose matrix is in close proximity to the surface of the indicating electrode, which is preferably platinum, gold or carbon. Most preferably, the indicating electrode is platinum. The substrate and oxygen diffuse into the enzyme layer, and react with the enzyme to produce the oxidized form of the substrate and hydrogen peroxide. Some of the hydrogen peroxide diffuses to the electrode, where it is oxidized electrochemically, liberating oxygen, protons and electrons. Thus, the current measured at the indicating electrode is related to the concentration of the analyte in the bioreactor solution.

Figure 5:
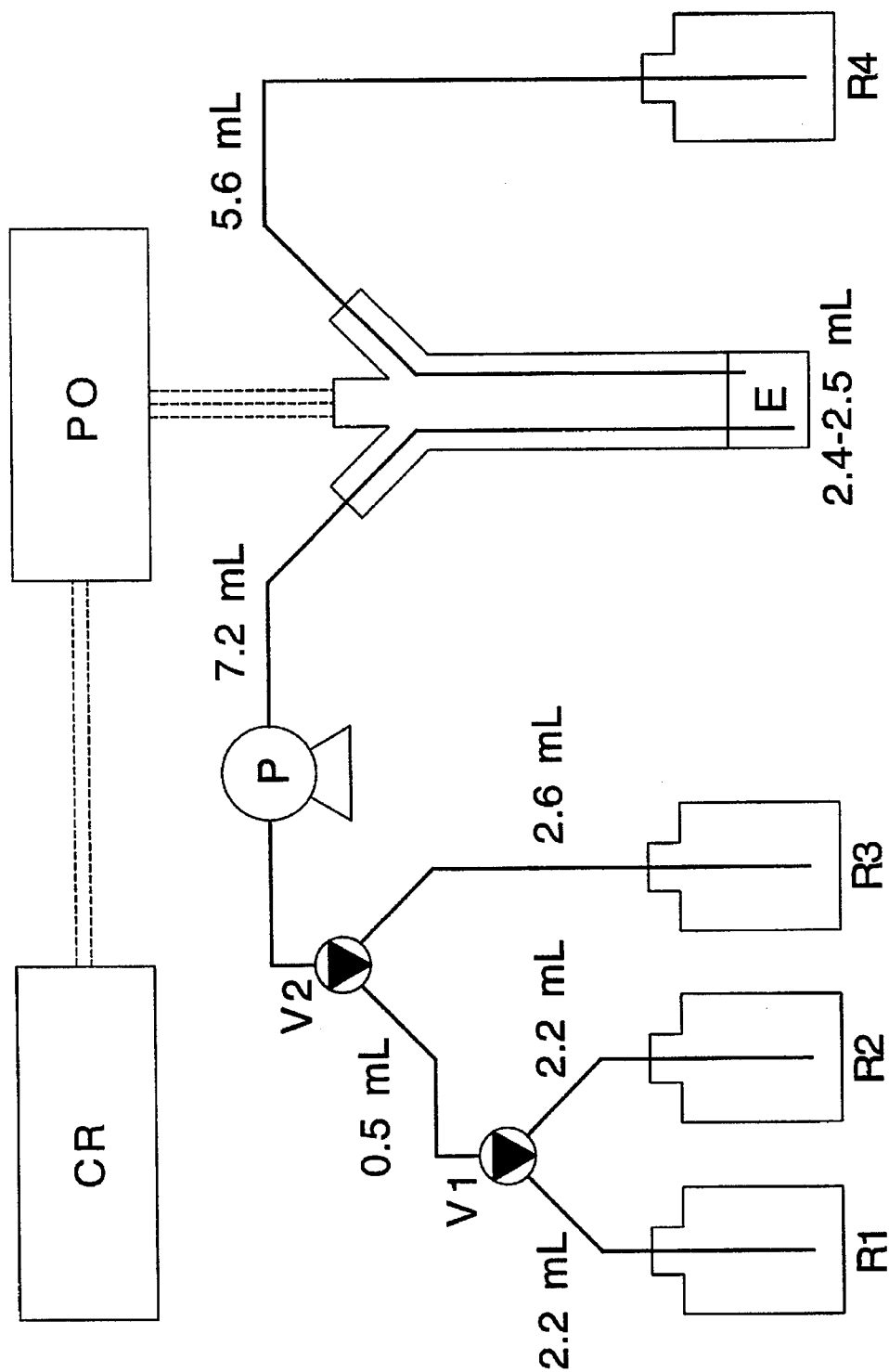
FIG. 5 is a schematic representation of a biosensor probe showing a reagent flow system and instrumentation.

A peristaltic pump was used to pump the appropriate reagent solutions through the inlet conduit into the biosensor probe body. In a preferred embodiment, a combination of three-way valves was used to select the reagent to be pumped. The three reagent reservoirs contain (1) the internal electrolyte and washing buffer (R1), (2) protein-CBD conjugate (R2), and (3) the elution buffer (R3) and, if necessary, the electrode performance may be regenerated by anodizing/cycling the electrode in an appropriate electrolyte. This pump system may be interfaced with a personal computer. FIG. 5 is a schematic representation of a reagent flow system, however a reservoir for the substrate (for example glucose) standard, for internal calibration is not shown. If an internal calibration standard is required, a third multi-port valve can be configured enabling a fourth reagent reservoir (R4) to be connected into the inlet conduit stream. Alternatively, a single, six-way valve could accommodate all the necessary solutions to be switched into the flow stream. A range of electronically-activated multi-port valves are commercially available. Adapting the biosensor of the present invention to a closed-loop system is well within the skill of an artisan in computer science, and does not require any inventive ingenuity beyond this disclosure. The valve system of the reagent reservoirs can be actuated by computer-controlled electric or pneumatic actuators (not shown) which allows, with the interface of the pump system with a personal computer, complete automated, on-line, closed-loop control of the reaction conditions. In addition, the operation of raising and lowering the internal electrode assembly, instead of being performed manually by turning a knurled knob on a threaded shaft, may be conducted within the scope of the present invention by a computer-controlled stepper motor. The sensor output is monitored by a personal computer rather than a chart recorder and the data used in computer algorithms for sensor calibration, self-diagnosis and regeneration as well as feedback control algorithms for bioprocess control.

It will also be appreciated that the biosensor disclosed herein is not limited to use with any particular enzyme catalyst. Any other enzyme reacting with specific substrates to produce hydrogen peroxide for generating an electrical signal functionally related to the presence of such specific substances may be used. Suitable enzymes include, but are not limited to, glucose oxidase, L-lactate oxidase, alcohol oxidase, galactose oxidase, cholesterol oxidase, pyruvate oxidase, uricase, aldehyde oxidase, xanthine oxidase, choline oxidase, acetylcholine esterase, L-glutamate oxidase, L-glutaminase, glucoamylase, amyloglucosidease, invertase and mutarotase.

In addition, the biosensor disclosed herein is not limited to electrochemical detection mechanisms. For example, optical mechanisms may be used, in which case the conjugate may comprise proteins other than enzymes.

B. Interface Membrane

In accordance with a second aspect of the present invention, an interface membrane is provided which comprises a supporting mesh, a perfluorosulfonic acid polymer impregnated substrate and a homogenous film of perfluorosulfonic acid polymer. The product so formed is a roughly lamellar structure with a base support, an inner substrate/perfluorosulfonic acid polymer layer and a homogenous perfluorosulfonic acid polymer film that is the outermost layer and forms, when the membrane is in place, an autoclavable biocompatible interface between the biosensor and the bioreactor environment.

Preferably, the substrate is selected from the group comprising ultrafiltration membranes such as cellulose acetate(s) (including cellulose triacetate), polysulfone, and Amicon PM series non-cellulose membranes, dialysis membranes such as those of regenerated cellulose, cellulose acetate(s), nitrocellulose, poly(vinylchloride) and various other porous or continuous (ie., non-porous) polymer membranes or films. Most preferably the substrate is cellulose triacetate.

The supporting mesh may be any suitable material able to withstand autoclave temperatures. Preferably the supporting mesh is a metallic screen (eg., stainless steel, aluminum, copper, silver, gold, etc.), a polymeric screen (eg., poly(vinylchloride), poly(tetrafluoroethylene), polystyrene, polycarbonate, or other fibrous filter material such as cellulose.

A schematic representation of the preferred interface membrane is provided in FIG. 3. The assembly of the membrane onto a biosensor is shown schematically in FIG. 4.

There are several important features of the interface membrane of the present invention:

1. Selective permeability—Nafion membrane/films are essentially non-porous (so there is no "pore size" per se). The perm-selectivity derives primarily from the morphology of the insoluble (ie., cast) membrane/film which, in turn, derives from the casting conditions. The other property that contributes to the perm-selectivity is the charge; Nafion is negatively charged, and hence tends to reject anionic species. The permeability properties of the invention have been found to be almost ideal for fermentation monitoring.

2. Biocompatibility—This is a very ambiguous term, but in the context of bioreactor monitoring, it basically means that: 1) cells tend not to stick to the material; 2) proteins or other biological macromolecules do not tend to stick to the material; 3) the material does not release chemicals (eg., solvent residues or polymer degradation products) or react with medium components to form products that are harmful to cells or harmful as a contaminant of the final bioprocess product. The interface membrane of the present invention has been proven to be biocompatible.

3. Sterilizability—the interface membrane must be able to withstand steam sterilization (ie. autoclaving), since this is the biotechnology industry's only acceptable sterilization protocol for bioreactors. The membrane of the present invention is autoclavable. In other applications, however, other sterilization protocols may be commonplace (eg., ethylene oxide gas, radiation, various solvents). It is expected that the interface membrane (of the invention) could also withstand these other treatments (with the exception of ethylene oxide).

4. Detachability—In other applications of Nafion, the membrane was cast directly over the electrode (and other overlying membranes/films) without any intervening structural material to permit separation of the interface membrane system from the rest of the sensor components. Previously, it was not contemplated to achieve this separation without degrading the performance of the ensemble system. The present invention successfully provides this advantage.

It is understood that the interface membrane described herein is a separate product from the biosensor described hereinabove. The interface membrane is a separate unit which may be suitably engaged with any biosensor system. It may be produced and sold as a disposable "cartridge" for use with any ensemble biosensor system including the biosensor systems described herein.

C. Method of Preparing Interface Membrane

In accordance with the third and final aspect of the present invention, a method of preparing a selectively permeable interface membrane comprises fixing a substrate onto a supporting mesh to form a substrate membrane, casting a perfluorosulfonic acid polymer film on the substrate membrane and curing the product so formed.

As an additional step, an appropriate hardware fixture must be selected or designed which permits the assembled membrane system to be attached to a biosensor. A preferred form of the present invention the hardware fixture comprises stainless steel or brass along with plastic, autoclavable components configured as shown schemically in FIG. 4. A supporting mesh is selected from those disclosed hereinabove. In the most preferred form, the supporting mesh is a stainless steel woven mesh with less than 100 um pores, although the port size is relatively unimportant and may range up to a few mm. An appropriate substrate material is selected from the group disclosed hereinabove. In a preferred form, this material is cellulose triacetate, most preferably, of the kind and more fully provided commercially as Gelman Metricel G. A.—8 membrane filters with a maximum pore size of 0.2 um. This pore size ensures that an aseptic barrier is maintained even in the event of a breach in the Nafion membrane. It is to be understood, however, that larger pore sizes may be successfully employed, but may not be as successive in the event of a breach of the Nafion membrane.

In order to construct the interface membrane, the supporting mesh must be cut to fit the hardware fixture. The supporting mesh is then fastened to the hardware fixture such that the mesh work forms a screen covering a portal that, once in place in an assembled probe, locates the interface membrane at the required position and orientation with respect to the other components. The orientation of these components is best shown in FIG. 4. An appropriate size and shape of substrate material is then cut to fit over the supporting mesh work and fastened such that the substrate material is held in contact with the supporting mesh work over the entire area of the portal.

The casting and curing of the membrane may be performed as follows. A stock dispersion of Nafion polymer is prepared, preferably from a commercially available 5% solution (aldrich chemicals). In a preferred embodiment, this stock dispersion is 0.5% Nafion polymer diluted from the as-received stock in a 1:1 solution of isopropyl alcohol and distilled-deionized water. It is to be understood, however, that the Nafion concentration may vary higher than the as-received 5%, although as the concentration increases the sensor response may be slower and lower in amplitude.

One or more aliquots of the above dispersion is then applied to the surface of the substrate membrane prepared as described above so that, when the interface membrane system is in place in a biosensor, the dispersion will be exposed to the analyte medium. In a preferred embodiment, aliquots ranging from 15 uL to 300 uL may be used and applied in one or two aliquots such that the entire surface of the substrate is covered. It is to be understood, however, that larger aliquots may be used depending on the size of the substrate area to be covered and the concentration of the casting dispersion.

The interface membrane is thereby formed by allowing the casting dispersion solvents to evaporate. In a preferred embodiment, this is carried out at room temperature and atmospheric pressure with the membrane/substrate/fixture remaining stationary in an orientation where the planar surface of the cast membrane is kept level in order to yield a uniform membrane/film over the surface of the substrate. It is to be understood, however, that environmental conditions may be varied over a considerable range.

The interface membrane so casted is then allowed to cure. Preferably, the curing time is at least 24 hours, most preferably even longer prior to autoclaving or any first exposure to a solution environment. Preferably curing is allowed to proceed at room temperature and atmospheric pressure for at least two to three days.

EXAMPLE 1

Synthesis of Protein Conjugate of Glucose Oxidase and CBD

The enzyme glucose oxidase (GOx) was conjugated with the cellulose binding domain from the cellulase exoglucanase from *Cellulomonase fimi*. More specifically, a chemically conjugated GOx-CBD protein was synthesized using the bifunctional cross-linking agent glutaraldehyde.

Glucose oxidase (EC 1.1.3.4) was Type X from *A. niger* (Sigma Chemical Co., St. Louis, Mo.) and was used without further purification. The cellulose binding domain from *C. fimi* exoglucanase ($CBD_{cex}$) was harvested from recombinant *E. coli* and purified according to methods described elsewhere (Ong et al., 1993[23]). $CBD_{Cex}$ antiserum was produced in rabbits (Whittle et al., 1982[24]). Grade 1 glutaraldehyde, 25% aqueous solution (Sigman Chemical Co.) was used as received for the GOx-CBD conjugation. The synthesis, purification, and storage of the GOx=CBD conjugate was carried out in 50 mM potassium phosphate buffer, pH 7. Cellulose powder (Avicel, type PH101, FMC International Food & Pharmaceutical Products, Cork, Ireland), washed with distilled water and phosphate buffer, was used for purification of the GOx-CBD conjugates. All other chemicals were analytical grade and used as received.

[23] Ong, E.; Gilkes, N. R.; Miller, R. C. Jr.; Warren, R. A. J.; Kilburn, D. G. The Cellulose-Binding Domain (CBD$_{Cex}$) of an Exoglucanase From *Cellulomonas fimi*: Production in *Escherichia coli* And Characterization of the Polypeptide. *Biotech. Bioeng.* 1993, 42, 401–409.

[24] Whittle, D. J.; Kilburn, D. G.; Warren, R. A. J.; Miller, R. C. Jr. Molecular Cloning of a *Cellumonas fimi* Cellulase Gene in *Escherichia coli*. *Gene* 1982, 17, 139–145.

A 10 mg/mL solution of glucose oxidase in 50 mM phosphate buffer, pH 7, was first activated with glutaraldehyde using a 50-fold excess of glutaraldehyde for each amino group (lysine residue or N-terminus) on the enzyme (Gibson and Woodward, (1992[25]). 40 μL of glutaraldehyde (25% aqueous solution) was added per mL of GOx solution. After incubation overnight at 4° C., the excess glutaraldehyde removed by dialysis versus phosphate buffer using Spectra/Por 2 dialysis tubing, MWCO 12–14 kD (Spectrum Medical Industries, Inc., Los Angeles, Calif. U.S.A.). Dialysis was performed for 24 hours versus 0.25 L of 50 mM phosphate buffer per mL of activated GOx solution. The dialysis buffer was changed after 12 hours. CBD$_{Cex}$ was added in a 1:1 molar ratio based on glucose oxidase and incubated overnight at 4° C. 0.693 mL of 11.2 mg/mL CBD$_{Cex}$ stock solution was added per mL of activated GOx solution. The CBD binds to the activated GOx either via the single lysine residue present or via the N-terminus of the CBD polypeptide (Coutinho et al., 1992[26]; Hansen and Middelsen, 1991[27]) according to the net reaction:

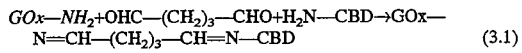

$$GOx-NH_2+OHC-(CH_2)_3-CHO+H_2N-CBD \rightarrow GOx- \\ N=CH-(CH_2)_3-CH=N-CBD \quad (3.1)$$

[25] Gibson, T. D.; Woodward, J. R. Protein Stabilization in Biosensor Systems. In *Biosensors & Chemical Sensors: Optimizing Performance Through Polymeric Materials*; Edelman, P. G., Wang, J., Eds.; ACS: Washington, DC, 1992; pp 44–55.

[26] Coutinho, J. B.; Gilkes, N. R.; Warren R. A. J.; Kilburn, D. G.; Miller, R. C. Jr. The Binding of *Cellulomonas fimi* Endoglucanase C (CenC) to Cellulose and Sephadex is Mediated by The N-Terminal Repeats. *Molec. Microbiol.* 1992, 6, 1243–1252.

[27] Hansen, E. H.; Mikkelsen, H. S. Enzyme-Immobilization by The Glutardialdehyde Procedure, An Investigation of The Effects of Reducing The Schiff-Bases Generated, as Based on Studying The Immobilization of Glucose Oxidase to Silanized Controlled Pore Glass, *Anal. Lett.* 1991, 24(8), 1419–1430.

Excess CBD was removed by buffer exchange with 50 mH phosphate buffer in an Amicon stirred cell using an Amicon PM30 (non-cellulose) membrane (Amicon Canada Ltd., Oakville, Ontario). Buffer exchange was performed until the absorbance (A$_{280}$) of the filtrate versus phosphate buffer approached zero. The GOx-CBD conjugate was then purified in a single step by binding to Avicel, using at least 150 mg of Avicel per mL of activated GOx solution. The conjugate was eluted from Avicel by washing twice with 0.1M NaCl in 50 mM phosphate buffer, and then one wash with de-ionized, distilled water. The final wash was saved and made up to 50 mM in potassium phosphate using 0.5M phosphate buffer. The purified GOx-CBD conjugate was stored in 50 mM phosphate buffer at 4° C. For longer term storage, the conjugate was stored bound to Avicel in 50 mM phosphate buffer at 4° C. and eluted when required. Batches of 1 mL and 10 mL volumes of GOX-CBD conjugate were prepared using this protocol.

In the conjugation protocol, distilled water was used for eluting the purified GOx-CBD conjugate from Avicel. The use of 8M guanidine HCl and 1M NaOH for elution, as suggested by Kilburn et al. (1992)[28], caused irreversible loss of enzyme activity. Using distilled water for elution, the soluble conjugation product was formed to retain greater than 60% of the activity of the original, unconjugated enzyme. In addition, the GOx-CBD conjugate retained by binding affinity of the CBD for cellulose, and exhibited GOx activity when bound to cellulose comparable to that of GOx immobilized by other techniques (Harrison et al., 1988)[29]. The conjugate could be adsorbed and desorbed from cellulose repeatedly, and could also be dehydrated for storage at room temperature, then reconstituted with PBS, pH 7.4, without a significant loss of activity. Non-specific binding of unconjugated GOx to Avicel or regenerated cellulose was found to be insignificant. The specific GOx activities of various samples of soluble GOx-CBD conjugate are shown in Table 1 to illustrate the typical stability of the conjugate over time. In glucose biosensor experiments using the GOx-CBD conjugate, it was found that the conjugate retained sufficient activity to be useful after up to 2 storage (when stored bound to Avicel).

[28] Supra at 21.

[29] Harrison, D. J.; Turner, R. F. B.; Baltes, H. P. Characterization of Perfluorosulfonic Acid Polymer Coated Enzyme Electrodes And a Miniaturized Integrated Potentiostat For Glucose Analysis in Whole Blood. *Anal. Chem.* 1988, 60, 2002–2007.

A potential alternative to chemical conjugation would be to develop an appropriate genetic construct that yields an active GOx-CBD fusion protein. Apropos of this, the gene encoding the glucose oxidase protein of *Aspergillus niger* has been cloned and expressed in yeast (Frederick et al., 1990[30]; DeBaetselier et al., 1991[51]). The main advantages of a genetically engineered conjugate would be greater uniformity and homogeneity of the conjugate reagent, as well as considerable simplification of large-scale conjugate production. A possible disadvantage, however, might be that the size and GOx-CBD ratio of the resulting conjugates could not be as easily tailored when compared to the chemical conjugation method, which may limit the efficacy of the GOx-CBD reagent.

[30] Frederick, K. R.; Tung, J.; Emerick, R. S.; Masiarz, F. R.; Chamberlain, S. H.; Vasavada, A.; Rosenberg, S.; Chakraborty, S.; Schopter, L. M.; Massey, V. Glucose Oxidase From *Asperigillus niger*: Cloning, Gene Sequence, Secretion From *Saccharomyces cerevisiae* and Kinetic Analysis of a Yeast-Derived Enzyme. *J. of Biol. Chem.* 1990, 265, 3793–3802.

[31] DeBaetselier, A.; Vasavada, A.; Dohet, P.; Ha-Thi, V.; De Beukelaer, M.; Erpicum, T.; De Clerck, L.; Hanotier, J.; Rosenberg, S. Fermentation of a Yeast Producing *A. niger* Glucose Oxidase: Scale-Up, Purification and Characterization of The Recombinant Enzyme. *Bio/Technology* 1991, 9, 559–561.

TABLE 1

Specific activity of various samples of soluble GOx-CBD conjugate. The specific activity was calculated from the results of GOx activity and total protein assays. The relative activity was determined compared to unconjugated GOx.

| Sample | Time in Storage | Conditions | Specific Activity (U/mg) | Relative Activity |
|---|---|---|---|---|
| Unconjugated GOx | 0 | Freshly prepared in 50 mM phosphate buffer, pH 7 | 118 | 100% |
| GOx-CBD Conjugate | 3 weeks | Purified on Avicel; eluted by | 68 | 58% |

TABLE 1-continued

Specific activity of various samples of soluble GOx-CBD conjugate. The specific activity was calculated from the results of GOx activity and total protein assays. The relative activity was determined compared to unconjugated GOx.

| Sample | Time in Storage | Conditions | Specific Activity (U/mg) | Relative Activity |
|---|---|---|---|---|
| Batch #2 | | distilled water after 1 week in storage | | |
| GOx-CBD Conjugate Batch #3a | 5 weeks | Unpurified | 91 | 77% |
| GOX-CBD Conjugate Batch #3b | 6 weeks | Unpurified | 72 | 61% |
| GOX-CBD Conjugate Batch #3a | 9 weeks | Purified on Avicel; eluted by distilled water after 7 weeks in storage | 30 | 25% |

EXAMPLE 2

Reversible Immobilization of Enzyme in Biosensor Using CBD Technology

In this glucose biosensor constructed from a platinum rotating disk electrode (RDE) with a cellulose matrix for enzyme immobilization via the CBD, a GOx-CBD conjugate was used. Using glucose standards, the biosensor is calibrated repeatedly in PBF during multiple cycles of loading and elution of the GOx-CBD conjugate in order to simulate the periodic regeneration of a glucose biosensor during a fermentation period.

Electrochemical data were obtained using a Pine AFRDE4 bi-potentiostat and a Pine AFMSRX analytical rotator (Pine Instrument Co., Grove City, Pa., U.S.A.). A Pine AFMDI1980 0.5 cm diameter platinum rotating disk electrode was fabricated in-house from 1.0 mm diameter platinum wire (Aldrich, Milwaukee, Wis., U.S.A.) bound in flint glass tubing (5 mm outside diameter) with epoxy (Chemgrip, Norton Co., Wayne, N.J., U.S.A.). A 25 mm×25 mm, 52 mesh platinum wire gauze (Aldrich) was crimped onto the platinum wire to increase the surface area of the counter electrode. The reference electrode was a saturated calomel electrode (SCE) (Fisher Scientific, Ottawa, Ontario, Canada, 13-620-52). A Kipp & Zonen Model BD112 strip chart recorder (Kipp & Zonen, Delft, Holland) was used for recording sensor output, and a Kipp & Zonen Model BD91 ZYY't recorder was used for recording cyclic voltammograms. The platinum working electrode (RDE) was prepared by polishing with 0.05 μm alumina and rinsing with distilled water. Immediately before each experiment, the working electrode was cycled in quiescent 0.5M $H_2SO_4$ from –0.26 V to +1.2 V at 100 mV/s for 10 minutes, anodized at +1.8 V for 10 minutes, then cycled again until a stable cyclic voltammogram was obtained.

The rotating disk electrode was modified using a retainer such that different cellulose matrices could be held in place over the platinum disk. The retainer was either a Teflon ring or a rubber ring (formed by cutting a transverse slice off the end of a piece of Tygon tubing) sized to fit tightly over the RDE. Three different cellulose-based membranes were used during the experimental biosensor trials: 1) Whatman No. 1 qualitative filter paper (Whatman International Ltd., Maidstone, England), 2) Spectra/Por 2 regenerated cellulose dialysis membrane, MWCO 12–14 kD (Spectrum Medical Industries Inc., Los Angeles, Calif., U.S.A.), and 3) nitrocellulose protein transfer membrane with 0.45 μm pores (Schleicher & Schuell, Keene, N.H., U.S.A.). The GOx-CBD conjugate was loaded by immersing the electrode assembly in a solution of GOx-CBD conjugate, followed by a single wash with 50 mM phosphate buffer.

The RDE was rotated at 500 rpm and potentiostated at +0.7V versus SCE in a 250 mL beaker with 100 mL of electrolyte. The electrolyte used in all biosensor experiments was phosphate buffered saline (PBS), pH 7.4, μ=0.2M (0.1M NaCl, 5 mM $NaH_2PO_4$, 30 mM $Na_2HPO_4$, preserved with 1 mM EDTA, and 5 mM sodium benzoate). The sensor was calibrated in PBS by recording the steady-state RDE current in response to a series of aliquots of glucose standard (0.1M glucose in PBS). The sensor response to decreasing concentrations of glucose was recorded by removing aliquots of the cell electrolyte and replacing with fresh, glucose-free PBS. Elution of the GOx-CBD conjugate was achieved by immersing the electrode assembly in the elution buffer, followed by a series of washes with 50 mM phosphate buffer only before reloading fresh GOx-CBD conjugate. Three different elution buffers were used: 1) distilled, deionized water, 2) 1M NaOH, and 3) 8M guanidine hydrochloride (99+%(CI) from Sigma Chemical Co., St. Louis, Mo., U.S.A.), prepared in 50 mM phosphate buffer and filtered through Whatman qualitative filter paper. All chemicals were analytical grade and used as received.

EXAMPLE 3

Regenerable Glucose Biosensor using CBD Technology

An Ingold $CO_2$ probe was used as the basis for the glucose biosensor. The Ingold probe was designed to withstand temperatures from 20°–125° C. and pressures from 0–2 bars. In its original configuration, the $CO_2$-permeable membrane was silicone rubber reinforced with a stainless steel mesh and a nylon net, mounted on a sterilizable plastic membrane cartridge with a stainless steel sleeve and a silicone rubber washed. The internal electrode was a glass pH electrode. The pH electrode was attached to a threaded shaft and could be raised from, and lowered to, the silicone membrane by turning a knurled knob at the end of the shaft. The probe body contained inlet and outlet tubes used for injecting electrolyte and pH calibration standards into the electrolyte chamber and was equipped with the necessary findings for insertion into the 25 mm side-ports of Chemap fermenters.

The basic hardware of the Ingold $CO_2$ probe had many of the features of the proposed glucose biosensor hardware described in the schematic diagram of FIG. 1, made available in a convenient, fermenter compatible package. Several modifications were performed to convert the Ingold probe to the prototype glucose biosensor:

1. A cellulose matrix was incorporated into the electrolyte chamber.
2. The silicone membrane was replaced with a custom designed electrode assembly with three electrodes for amperometric operation.
3. The internal pH electrode was replaced with a custom designed electrode assembly with three electrodes for amperometric operation.
4. To fit the new internal electrode unit into the probe body, a custom designed adapter was required to mount the electrode assembly onto the threaded shaft used for raising and lowering the internal pH electrode.
5. The syringes used for injecting electrolyte and pH electrode calibrant into the $CO_2$ probe were replaced with tubing, valves, and a peristaltic pump.
6. A replaceable interface (dialysis) membrane was prepared and attached to the probe body.

The cellulose matrix was a disk of Whatman No. 1 qualitative filter paper (Whatman International Ltd., Maidstone, England) cut to approximately 7 mm in diameter. The cellulose matrix was sandwiched between the internal electrode and the glucose-permeable outer membrane.

The internal electrode assembly was designed and built in-house. The three-electrode unit had an outside diameter of 6 mm and consisted of a Pt indicating electrode, Pt counter electrode, and Ag/AgCl reference electrode. The Pt indicating electrode was a 1.0 mm diameter platinum wire (Aldrich, Milwaukee, Wis., U.S.A.) in a glass shroud made from 4 mm O.D. flint glass tubing. One end of the glass tubing was partially closed by melting the glass over a Bunsen burner, such that the inside diameter was just greater than 1 mm. The platinum wire was then bonded into the glass using Chemgrip epoxy (Norton Co., Wayne, N.J., U.S.A.) to form a seal. The glass-shrouded platinum wire was ground and sanded with successively finer grades of sandpaper, followed by polishing to a mirror finish with 0.3 µm and 0.05 µm alumina, leaving exposed a circular platinum disk with a surface area of 0.785 $mm_2$.

The counter electrode and reference electrode were 1.0 mm diameter Pt and Ag wire, respectively (Aldrich, Milwaukee, Wis., U.S.A.), tightly coiled around the glass shrouded indicating electrode. The surface area of the counter electrode was much greater than the surface area of the indicating electrode to ensured that the area of the counter electrode was not charge transfer limiting. The Ag/AgCl reference electrode was fabricated by anodizing the Ag wire in the presence of $Cl^-$. The Ag wire was potentiostated at +0.2 V versus SCE for 8 hours, using a Pt wire counter electrode and an electrochemical cell containing 0.1M KCl.

Modem cable was used for the electrode leads, because the shielding of the individual wires in the modem cable allowed the reference electrode lead to be shielded from the other electrode leads. The electrode leads were attached to the electrode wires using gold crimps and soldered.

Immediately before use, the bare Pt indicating electrode was cycled in quiescent 0.5M $H_2SO_4$ from −0.26 V to +1.2 V at 100 mV/s for 10 minutes, anodized at +1.8 V for 10 minutes, then cycled until a stable cyclic voltammogram was obtained. For some experiments, described below, the indicating electrode was coated with cellulose acetate using a modification of the method described by Wang and Hutchins (1985)[32]. A 7.5 µL drop of 2.5% cellulose acetate (BDH Ltd., Poole, England) in a 1:1 solution of acetone and cyclohexanone (stirred for 12 hours) was applied to the indicating electrode and allowed to dry overnight. The indicating electrode was cyclced and anodized immediately before coating with cellulose acetate.

[32] Wang, J.; Hutchins, L. D. Thin-Layer Electrochemical Detector With a Glassy Carbon Electrode Coated With a Base-Hydrolyzed Cellulosic Film. *Anal. Chem.* 1985, 57, 1536–1541.

A stainless steel adapter was used to mount the internal electrode unit to the electrode shaft of the probe body. The flange on the adapter was designed to meet a shoulder inside the probe body to prevent the electrode shift from being inserted too far into the probe body. An O-ring was used between the adapter and the inside wall of the probe body to maintain a sealed internal chamber. An insulating wrap of black electrical tape was used between the electrodes and the adapter. Silastic adhesive was used to bond the internal electrode unit into the adapter and provide a liquid seal. The distance from the tip of the internal electrode unit to the flange on the adapter was set at 35 mm, such that the indicating electrode would contact the outer membrane when fully lowered. It was also necessary to bore the minimum inside diameter of the probe body from 8.13 mm to 9.55 mm.

Reagent flow system:

A Gilson Minipuls 3 peristaltic pump (Gilson Medical Electronics, Middleton, Wis., U.S.A.) was used to pump the appropriate reagent solutions through silicone tubing into the probe body. A combination of three-way valves, shown in FIG. 5, was used to select the reagent to be pumped. The three reagent reservoirs contained 1) the internal electrolyte and washing buffer, 2) glucose standard, for internal calibration, and 3) the elution buffer. The internal electrolyte and washing buffer was PBS (0.1M NaCl, 5 mM $NaH_2PO_4$, and 30 mM $NaH_2PO_4$, pH 7.4, µ=0.2M, preserved with 1 mM EDTA and 5 mM sodium benzoate). The elution buffer was PBS with 8M guanidine hydrochloride.

The protocols used for loading and eluting the GOx-CBD conjugate are listed below. Flow rate was calibrated against pump speed, and the volumes of the different segments of the flow system shown in FIG. 5 were determined by measuring the time required for a fluid to pass through the different segments at a given flow rate. The time required to wash all unbound GOx-CBD conjugate out of the enzyme chamber after the enzyme loading cycle was determined by collecting fractions of the effluent from the probe while washing the enzyme chamber with PBS. The presence of protein in the fractions was determined by measuring the absorbance at 28 nm versus fresh PBS. The time required to wash all traces of the guanidine elution buffer out of the enzyme chamber after the enzyme elution cycle was determined using the Pt indicating electrode as a detector for guanidine at the normal operating potential of +0.7 V versus Ag/AgCl. The enzyme chamber was washed with PBS until the sensor signal returned to baseline.

Enzyme loading protocol:
1. Raise the internal electrode assembly.
2. Pump GOx-CBD conjugate solution for 1.0 minute at 4.0 rpm (ie., 2.2 mls/min).
3. Pump PBS for 4.5 minutes at 4.0 rpm.
4. Stop flow for 1.0 minutes. At this point the bolus of GOx-CBD conjugate has filled the enzyme chamber.
5. Pump PBS for 7.5 minutes at 4.0 rpm to wash unbound conjugate from the enzyme chamber.
6. Lower the internal electrode assembly.

The GOx-CBD conjugate was pumped into the flow system by removing the inlet tubing from the PBS reservoir and inserting into a reservoir of conjugate. The soluble conjugate solution prepared for use in the enzyme chamber of the prototype biosensor was made 0.1M in NaCl to approximate the composition of the PBS electrolyte and satisfy the requirements of the Ag/AgCl reference electrode. Once a bolus of the GOx-CBD conjugate was loaded into the flow system, the tubing inlet was rinsed with distilled water and re-inserted into the PBS reservoir. PBS was pumped through the flow system to push the bolus of GOx-CBD conjugate into the enzyme chamber. The total time required for the loading protocol was 14.0 minutes.

Enzyme elution protocol:
1. Raise the internal electrode assembly.
2. Pump guanidine elution buffer for 2.5 minutes at 4.0 rpm.
3. Pump PBS for 2.0 minutes at 4.0 rpm.
4. Pump PBS for 5.5 minutes at 48.0 rpm (maximum pump rotation speed).
5. Lower the internal electrode assembly.

Separate tubing inlets were used for the guanidine elution buffer and the PBS wash buffer, controlled by a three-way valve. The total time required for the elution protocol was 10.0 minutes.

Dummy electrode:

In addition to the modifications described above, a stainless steel plug, or "dummy electrode", was fabricated so that the probe body could be steam sterilized in a fermenter with the internal electrode assembly removed. The internal electrode assembly as constructed could not be autoclaved or the Chemgrip epoxy would become brittle and crack. A dummy electrode was required as a plug when the internal electrode assembly was removed, in case failure of the probe membrane during steam sterilization released superheated steam through the electrode shaft.

EXAMPLE 4

Interface Membrane

A custom designed perfluorosulfonic acid (Nafion) membrane (Aldrich Chemical Company, Inc., Milwaukee, Wis., U.S.A.) was cast on a 0.2 μm Metricel GA-8 (cellulose triacetate) membrane filter (Gelman Instrument Co., Ann Arbor, Mich., U.S.A.). One coat of 250 μL of 0.5% Nafion (in 50/50 isopropyl alcohol in water) was solution cast on a 25 mm diameter membrane filter with a 50 μm stainless steel mesh for rigid support. The membrane filter and stainless steel mesh were secured onto the membrane cartridge with steel wire before casting the Nafion membrane. The Nafion solution was allowed to dry in air for at least 1 hour before the stainless steel sleeve was placed over the membrane cartridge and sealed with Silastic adhesive. The stainless steel mesh faced the interior of the membrane cartridge such that the Nafion coated membrane filter was on the exterior and would be in direct contact with the fermentation broth. It may be advantageous, under some circumstances to electrochemically "clean" the indicating electrode before loading fresh enzyme. Using this arrangement, a smooth Nafion coating could be cast on the outer surface which would likely behave in a more well-defined manner in a stirred solution than the steel mesh. The steel mesh would also provide structural support for the membrane during the high pressure steam sterilization of the fermenter.

In the original prototype, the silicone membrane of the $CO_2$ probe was removed by separating the steel sleeve from the plastic membrane cartridge and dissolving the silicone with silicone sealant removed (Dow Corning). The new interface membrane was draped over the membrane cartridge and secured using steel wire and/or silastic medical adhesive (Dow Corning). the steel sleeve was placed over the membrane and cartridge and sealed in place with silastic adhesive. Characteristics of the glucose-permeable outer membrane.

Table 2 lists the characteristics of a number of different membranes tested as possible glucose-permeable outer membranes for the prototype. Four properties were determined to be essential for the outer membrane:

1. The membrane must be autoclavable.

2. The membrane must be sufficiently permeable to glucose and oxygen so that the sensor response time is fast enough to follow changes in the glucose concentration in the medium. For example, a high cell-density cultivation of *E. coli* with an optical density of 40 (measured at 600 nm versus distilled water) can consume 2.5 g of glucose from 1 L of medium in approximately 10 minutes (D. Hasenwinkle and E. Jervis, unpublished results). A sensor response time of less than five minutes was considered adequate for the present work, although faster response times would certainly be advantageous.

3. The membrane must be impermeable to electroactive species which will contribute to a high background signal, as well as to medium components which will inhibit or denature the enzyme or poison the platinum surface of the indicating electrode over the course of a fermentation run.

4. The membrane itself must be resistant to fouling by protein or microbial adsorption (for example) over the course of a fermentation run.

A number of different membranes were comparison tested to the interface membrane of the present invention. Candidate membranes were chosen on the basis of structure, strength, molecular weight cut-off, availability and ease of use. Non-cellulose membranes were chosen where possible to prevent conjugate binding to surfaces other than the intended cellulose matrix and thereby simplifying the system of experimental variables:

(i) Spectra/For 2 dialysis tubing from regenerated cellulose, MWCO 12–14 kD, cut lengthwise to form a flat sheet (Spectrum Medical Industries, Inc., Los Angeles, Calif., U.S.A.);

(ii) Amicon PM10 (MWCO 10 kD) and PM30 (MWCO 10 kD) non-cellulose ultrafiltration membranes with support backing (Amicon Canada Ltd., Oakville, ON, Canada).

(iii) Filtron Omega 10 (MWCO 10 kD), polysulfone ultrafiltration membrane with support backing (Filtron Technology Corporation, Northborough, Mass., U.S.A.); and (iv) A custom-designed perfluorosulfonic acid (Nafion) membrane in accordance with the present invention.

TABLE 2

Characteristics of different membranes tested as potential outer membranes for the glucose biosensor prototype

| Dialysis Membrane | MWCO (kD) | Steam sterilizable? | Performance rating in complex medium | Response time (min) |
|---|---|---|---|---|
| None | — | — | — | 5 |
| Spectra/Por 2 | 12–14 | Yes | — | 12 |
| PM30 | 30 | No | Poor | 6 |
| PM10 | 10 | No | Fair | 25 |
| Omega 10 | 10 | No | — | $\infty$[1] |
| Nafion | — | No | Fair | 10 |
| Nafion (autoclaved)[2] | — | No | Fair | 3 |
| Nafion (autoclaved)/Cellulose Acetate[2,3] | — | No | Excellent | 5 |

[1]The sensor did not respond to glucase in the concentration from 0–23 mM with this membrane.
[2]The membrane cartridge with the Nafion membrane was submerged in PBS and autoclaved before testing.
[3]This notation refers to the combination of a Nafion membrane on the membrane cartridge (the glucose-permeable outer membrane of the sensor) and a cellulose acetate coating on the surface of the indicating electrode.

No off-the-shelf membrane tested could satisfy all of the required conditions listed above. A custom membrane was designed using a solution of perfluorosulfonic acid (Nafion) cast on a 0.2 μm cellulose triacetate membrane filter with a 50 μm stainless steel mesh. Nafion has been used with good results as a dialysis membrane material on GOx/Pt electrodes for the determination of glucose in whole blood (Harrison et al., 1988). The permselectivity of Nafion is due to the rejection of anionic species by the negatively charted perfluorinated ionomer membrane, as well as the specific morphology of the membrane. The sterizability of the Nafion membrane is discussed below. The 0.2 μm membrane filter acted as a support for casting the Nafion membrane, and also ensured that a sterile barrier was maintained in case of failure of the Nafion coating. The stainless steel mesh provided rigid support.

EXAMPLE

Performance of Interface Membrane

By far, the most demanding conditions in which the candidate membranes will be used are the conditions of a real fermenter run, due to the presence of cells, cellular metabolites, proteins, and other medium components. Not only must the membrane be autoclave and enable a fast sensor response time, but the membrane must contribute to stable sensor operation over the course of the entire fermentation. The potential of each membrane to perform satisfactorily in the fermentation environment was evaluated in 150 mL beaker experiments using Luria broth as a complex medium for testing. The prototype sensor with a given membrane was first calibrated in PBS and the response time to the addition of aliquots of glucose was noted (Table 2). The electrolyte was then immediately changed to Luria broth and the sensor was recalibrated in order to assess the performance of the given membrane in complex medium. The time between obtaining the two calibration curves was minimized to less the possible effect of enzyme deactivation on the sensitivity of the second calibration curve. The addition of Antifoam C to the Luria broth was found to have no effect on the sensor signal at steady state.

In order to compare the results of a series of experiments using different membranes on the same graph, the sensor calibration curve established in PBS for each sensor configuration was normalized with respect to the maximum sensor current (i.e., at 23 mM glucose) to give a maximum dimensionless sensor current of 1. The calibration curve in Luria broth from a given experiment was then expressed relative to the calibration curve in PBS by normalization with the same value, since the only experimental variable changed was the electrolyte/medium.

Figure 7:
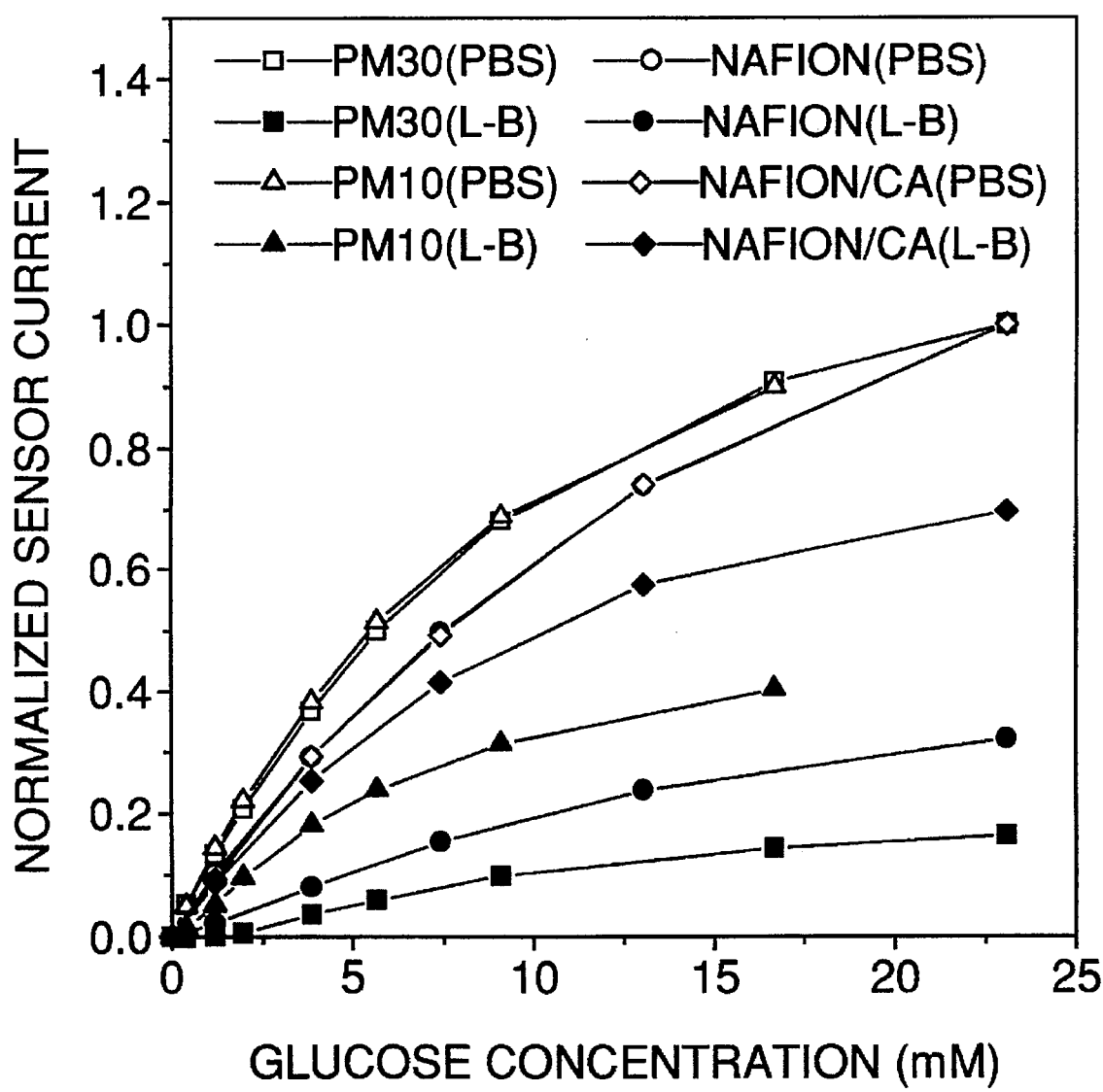
FIG. 7 is a graph representing normalized calibration data for a biosensor in PBS and Luria broth (LB) using the interface membrane of the present invention both before and after autoclaving.

It can be seen from the results in FIG. 7 that, in all cases, significant signal attenuation and sensitivity loss was observed in complex medium compared to defined medium (ie., PBS). This phenomenon has been reported for other enzyme electrodes, as well as ion-selective electrodes, mass spectrometers, and gas chromatographs. Although not completely understood, the observations are attributed to effects of the analyte matrix. A number of possible explanations have been forwarded, however the phenomenon may be due to more than one chemical effect, or a symbiosis of several different effects:

1. It is the activity and not the concentrations of the analyte that is measured by chemical sensors. The equality of concentration and activity is true only at infinite dilution. The presence of additional molecular species, as in fermentation media, may reduce the activity of the analyte.
2. Low-molecular weight molecules may complex with macromolecules in biological media, thereby reducing the chemical activity with respect to concentration, the mass transfer through the sensor membrane, or affinity of the enzyme for the substrate.
3. Proteins, lipids, and other hydrophobic components of biological media may occupy a non-aqueous compartment of the solution which is not accessible to the analyte. Thus the volume occupied by the analyte is lower than the total volume. This does not necessarily explain the observed signal attenuation and loss of sensitivity, but may explain the poor correlation in analytical results obtained by different techniques.
4. Changes in the compositions of the liquid phase may change the properties of mass transfer through membranes significantly. For example, the partitioning coefficient of the membrane/solution interface may differ depending on the solution. Protein or microbial adsorption to the membrane may increase the mass transfer resistance of the membrane.

5. In the case of enzyme electrodes, components of the medium may inhibit or denature the enzyme or poison the electrode, causing a decrease in the measured sensor signal or a loss of sensitivity. For example, competitive inhibition of glucose oxidase by D-glucal (a substrate analog) and/or halide ions ($Cl^-$, $Br^-$, $I^-$) has been reported. The immobilization of the enzyme was thought to prevent the inhibitory effect of $Cl^-$ ion.) In addition, other components of the medium, such as ascorbate, are known to adsorb to platinum surfaces, forming a monolayer which blocks electrochemical reactions at the surface, thereby attenuating the sensor signal and eventually poisoning the electrode.

6. In the case of oxidase enzyme-based systems, the analyte matrix may affect the activity or concentration of dissolved oxygen, which is required as the electron acceptor for the reduced form of the enzyme cofactor $FADH_2$. The solubility of oxygen, for example, is reduced by high concentrations of ionic species.

Figure 6:
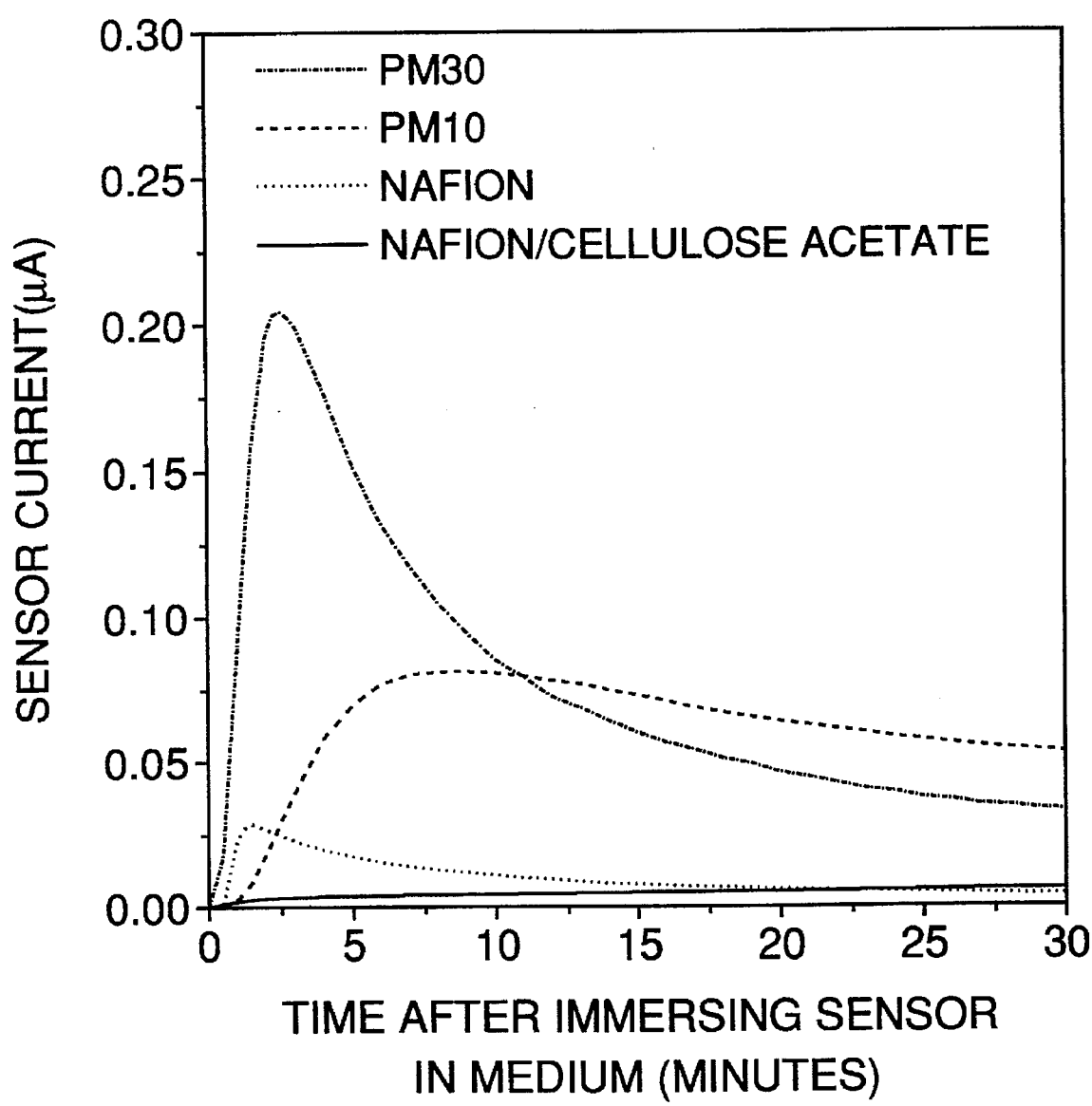
FIG. 6 is a graph representing a comparison of biosensor equilibration time in Luria broth of an interface membrane system of the present invention and other membranes.

FIG. 6 shows the equilibration time of the prototype sensor when inserted into Luria broth, before the addition of glucose. All of the membranes tested, except the Nafion/cellulose acetate combination, demonstrated on initial current response peak which then decayed to a stable background. Although the mechanism for this behaviour is not clear, the initial peak in response was attributed to the oxidation of electroactive species in the medium, and the subsequent decay of the peak was through to be a result of membrane fouling and/or electrode poisoning by adsorption of proteins or other species in the medium. The absence of the initial response peak in the case of the Nafion/cellulose acetate combination membrane may have been due to the protective cellulose acetate coating on the indicating electrode and the permselective properties of the Nafion membrane. The Nafion/cellulose acetate combination membrane also established the lowest background signal compared to the other membranes investigated, indicating a high rejection of interfering species, as expected.

Figure 8:
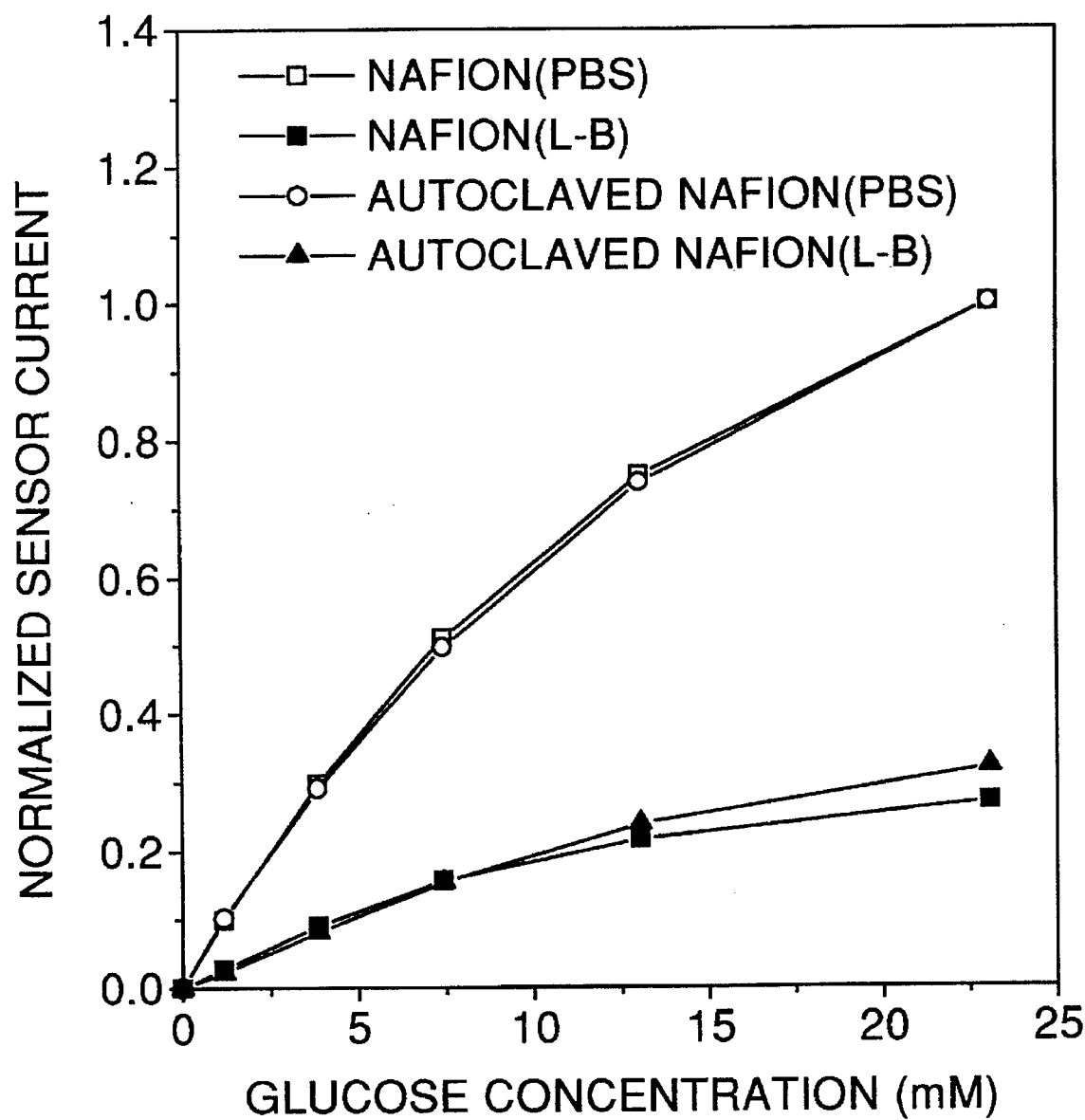
FIG. 8 is a graph representing the normalized calibration data for the prototype sensor in PBS and Luria broth (LB) using Nafion membrane before and after autoclaving.

These characteristics, in addition to the relatively fast sensor response time and low signal attenuation and sensitivity loss in Luria broth (refer to FIG. 7), pointed to the Nafion/cellulose acetate membrane system as the best choice (among the membranes investigated here) for use in the biosensor protype during glucose monitoring of a real fermentation. The sterilizability of the Nafion membrane was established by autoclaving the membrane cartridge while submerged in PBS. After autoclaving the membrane and recalibrating the sensor in PBS, the sensor response time was found to have decreased from 10 minutes to 3 minutes. This may have been due to the dissolution of a small fraction of the Nafion coating during the high temperature process of autoclaving (Moore and Martin, 1986), resulting in a decrease in mass transfer resistance in the membrane and a faster sensor response time. Most importantly, however, FIG. 8 demonstrates that the performance of the autoclaved Nafion membrane in complex medium was not significantly affected.

Figure 9:
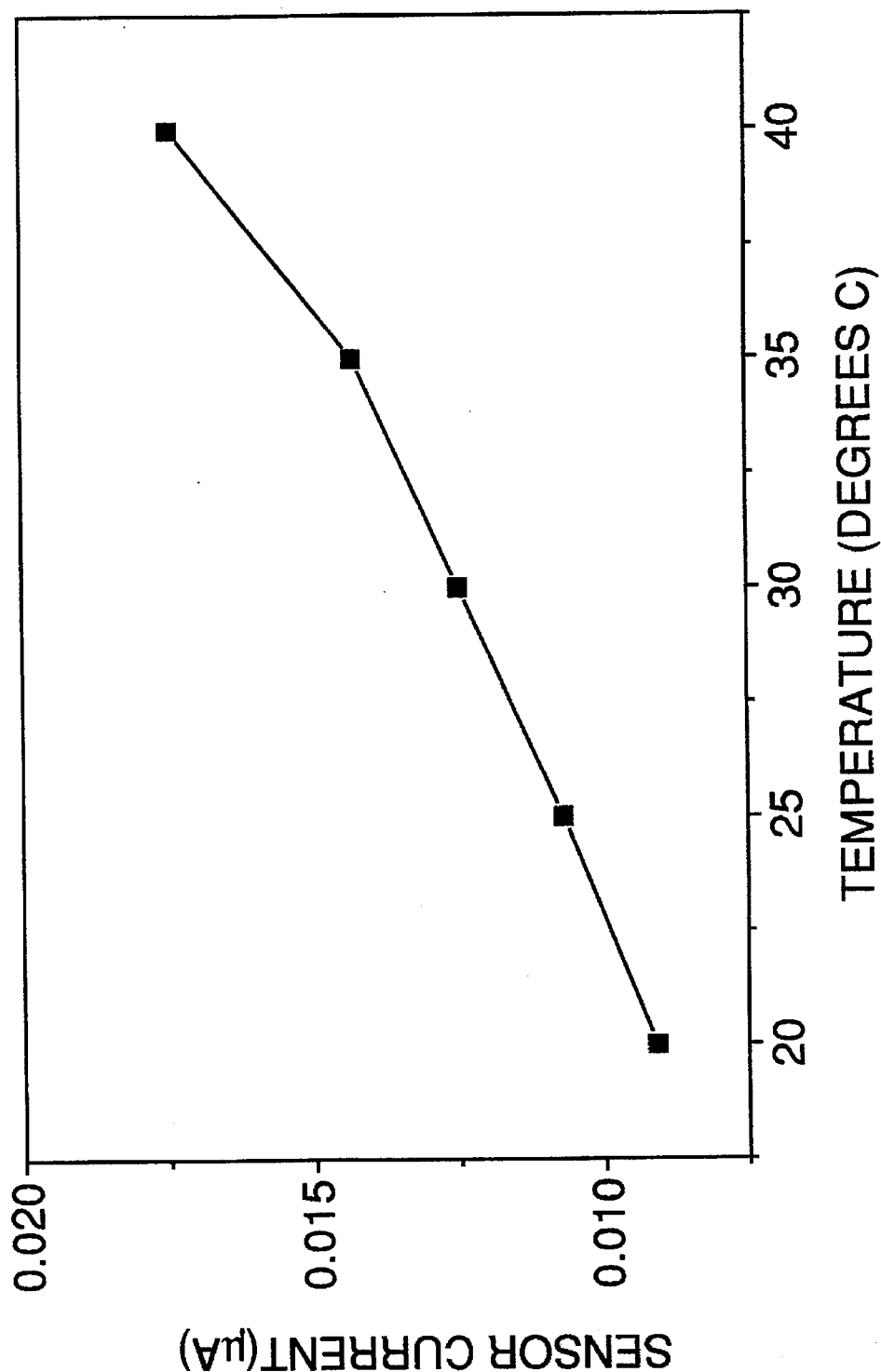
FIG. 9 is a graph representing the effect of temperature on the biosensor signal at steady state.

Effect of temperature and pH:

Using the Chemap fermenter control unit and the 3.5 L fermenter, a number of fermenter operating parameters could be varies to investigate the effects on the sensor signal at steady state. The effect of temperature was investigated over the range of normal operating temperatures for industrial fermentations (see FIG. 9). A direct relationship between the sensor signal and temperature was expected due to temperature dependent increases in the reaction rate constant and the diffusion coefficient, as predicted by Arrhenius' law and the Stokes-Einstein equation, respectively. However, the decrease in medium dissolved oxygen concentration at higher temperatures (as a result of lowered oxygen solubility) may also have reduced the sensor signal due to limitation of the enzyme kinetics. At temperatures greater than 40° C. the enzyme glucose oxidase is reported to be unstable (Nakamura et al., 1976). Fortier et al. (1990) have investigated the effect of temperatures greater than 40° C. for glucose oxidase immobilized in polypyrrole on a Pt electrode and reported a decrease in sensor current, due to temperature-induced denaturation of the enzyme. However, the effect was found to be reversible up to a temperature of 50° C.

Figure 10:
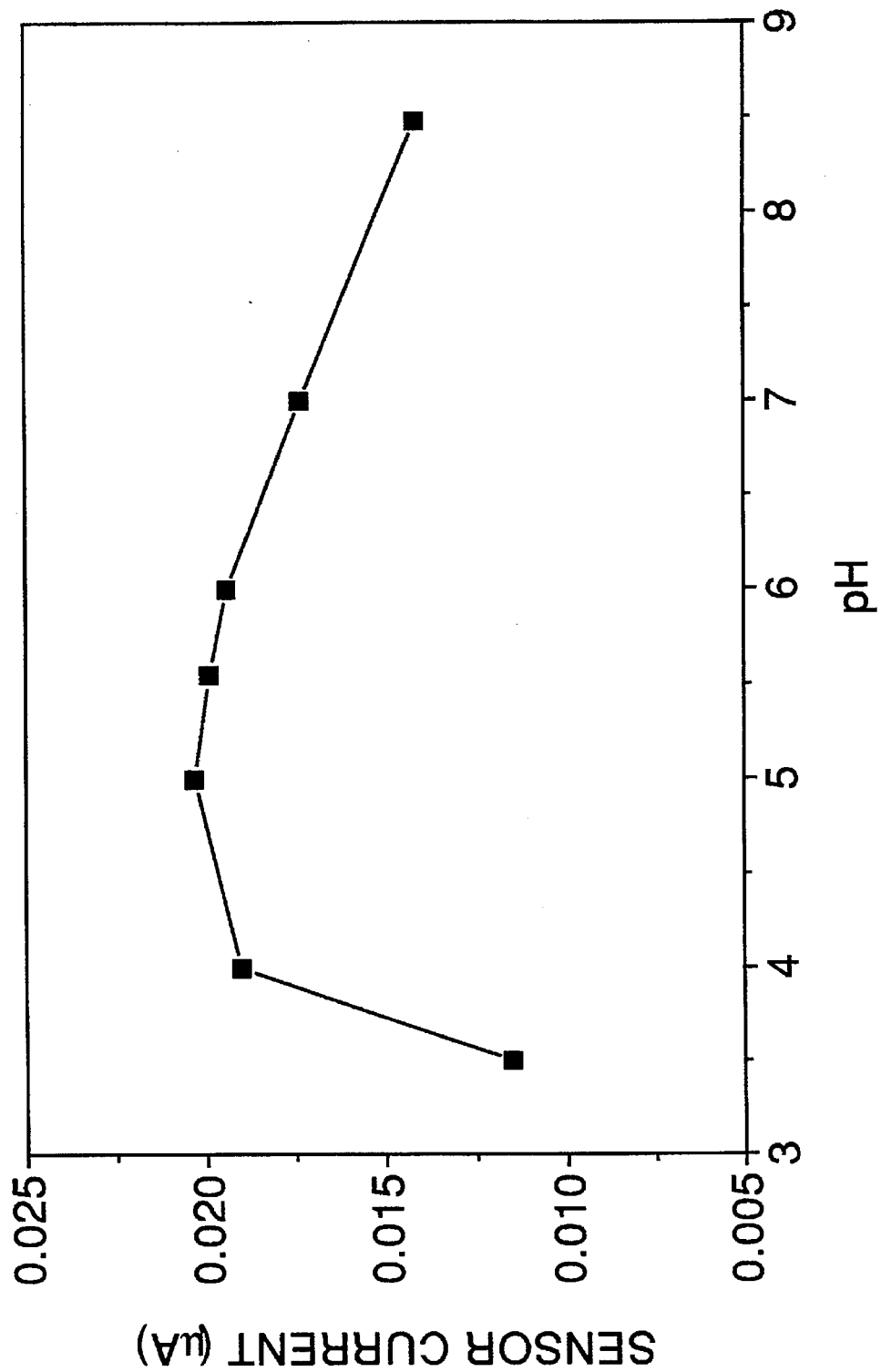
FIG. 10 is a graph representing the effect of pH on the biosensor signal at steady state.

The effect of medium pH on the steady-state sensor signal is shown in FIG. 10, which demonstrates a maximum at pH 5. The pH sensitivity of the sensor is largely due to the pH dependence on the enzyme activity itself.

Figure 11:
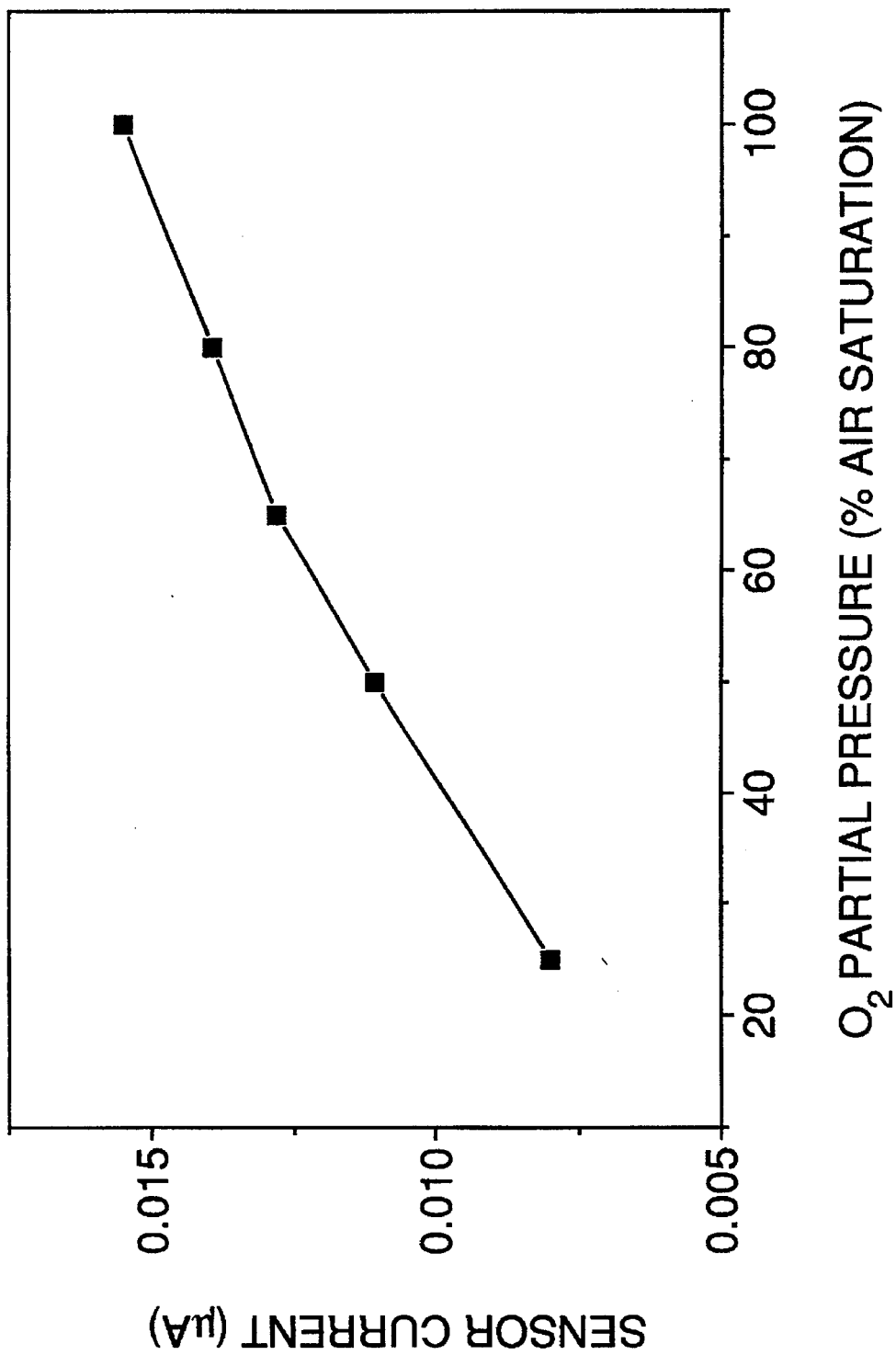
FIG. 11 is a graph representing the effect of dissolved oxygen tension on the biosensor signal at steady state.

Effect of medium dissolved oxygen tension, stir rate, and air flow rate:

The effect of medium dissolved oxygen tension was investigated in the 3.5 L fermenter by sparging the fermenter simultaneously with nitrogen and air and adjusting the flow rates of the two gases to control the medium dissolved oxygen at various levels. A direct relationship was observed between dissolved oxygen level and the steady-state sensor signal (see FIG. 11). The requirement for oxygen as the electron acceptor to turn over the reduced form of the flavin group of glucose oxidase during the oxidation of glucose is known. At high dissolved oxygen concentrations, where the enzyme kinetics are glucose limited, variations in the dissolved oxygen level are not critical. The effect of medium dissolved oxygen on the sensor output becomes important in fermentations where the dissolved oxygen level experiences large fluctuations. From FIG. 11, it can be seen that a constant dissolved oxygen concentrations would have to be maintained in order to eliminate the dissolved oxygen dependence of the sensor output.

Dissolved oxygen control during a fermentation is easily accomplished using currently available technology for feedback control of aeration and stir rate. The effect of variation of stir rate and air flow rate on the steady-state sensor signal was investigated in the 3.5 L fermenter. The sensor prototype was found to be insensitive to stir rate over the range from 300 to 500 rpm. A 3% change in the steady-stage signal was observed over the range from 20 to 200 rpm, indicating that the sensor signal was limited to a small extent by external mass transfer resistance in this range. At zero stir rate, the sensor signal began to increase, which was attributed to $H^2O^2$ accumulation in the enzyme chamber. Experiments with aeration demonstrated a 1–2% decrease in the steady-state signal with the initialization of air flow, but no further change was observed over the range of air flow rates from 3 to 7 L/min. It should be noted that these observations were recorded for the prototype sensor using the Nafion/cellulose acetate membrane system. The results are dependent on the sensor configuration and the mass transfer properties of the membrane system, however, and as part of the process of optimization of the prototype, the sensor response should be re-characterized following each design change.

As the medium dissolved oxygen was exhausted, a significant decrease in the sensor response was observed and the signal approached zero (data not shown). This may have been due to depletion of dissolved oxygen in the enzyme chamber by enzymatic consumption and/or mass transfer into the fermenter medium through the sensor membrane. Glucose oxidase electrodes which depend on oxygen as the electron acceptor cannot be used in anaerobic environments unless oxygen is provided by some internal source within the probe body (eg., an oxygenated buffer flow stream), or substitute electron acceptors, such as ferrocene derivatives, are used in place of oxygen to mediate the electron transfer from the enzyme to the electrode.

EXAMPLE 6

Glucose Monitoring During Fed-Batch Cultivation of E. coli

Cultivation of E. coli was performed in a 20 L fermenter for the purpose of monitoring glucose concentration with the glucose biosensor prototype. The probe body was sterilized in situ but the internal electrode assembly was removed to prevent degradation of the Chemgrip epoxy used to bond the indicating electrode into the glass shroud. If this had occurred, liquid leakage into the glass shroud around the indicating electrode would have caused undesirable variations in the electrode current due to the exposure of electrochemically active internal materials contacting the Pt electrode. Other high-temperature adhesives must be investigated to replace the Chemgrip epoxy in the internal electrode assembly if the electrode is to remain inserted in the probe body during sterilization (although this may not be essential). The Nafion/cellulose acetate membrane system was used.

The COx-CBD conjugate was loaded using the enzyme loading protocol described above, and the sensor was calibrated before inoculation by adding a known amount of glucose to the medium in a series of aliquots. The sensor calibration curve was determined by comparing the steady-state sensor signal after each aliquot to the calculated glucose concentration in the fermenter. The Michaelis-Menten equation was fitted to the sensor calibration curve and used as a conversion function to calculate the medium glucose concentration from the measured sensor signal during the fermentation. The sensor response time was five minutes or less.

After 8 hours, the enzyme was eluted and reloaded in situ. The internal electrode unit was lowered into contact with the cellulose matrix after elution of the enzyme to measure the background signal. During this phase (ie., the second enzyme loading of the prototype) the background signal was used as the baseline for recalibration of the sensor after reloading fresh GOx-CBD conjugate. Ideally, the sensor would be recalibrated at this point using internal calibration standards pumped into the enzyme chamber. The sensor was recalibrated by adding four aliquots of glucose to the fermenter, and the steady-state sensor signal was compared to the results of off-line glucose analysis of medium samples (taken once the sensor signal had reached steady-state). This method is not ideal, as the inaccuracies of the off-line glucose analyzer are incorporated into the calibration curve. In addition, the medium glucose concentration is changing during the calibration due to cellular metabolism. However, the sensor response time in this experiment was relatively fast, and it was found that steady-state sensor signals could be obtained within a sufficiently short period of time to obtain a useful calibration.

The fermentation run was carried out for a total of 16.5 consecutive hours. Furthermore, the experiment was not terminated due to failure or deterioration of the probe. The longest experiment reported in the literature (to this author's knowledge) involving glucose monitoring during a fermentation with an in situ enzyme electrode probe is 12 hours (Cleland and Enfors, 1983)[33]. Most of the experimental results reported in the literature ranged from 36 minutes to 5 hours of operation. The longevity of this experiment is attributed to the stability of the biosensor prototype provided by the Nafion/cellulose acetate membrane system and the capacity for in situ enzyme replacement.

[33] Supra at 15.

Figure 12:
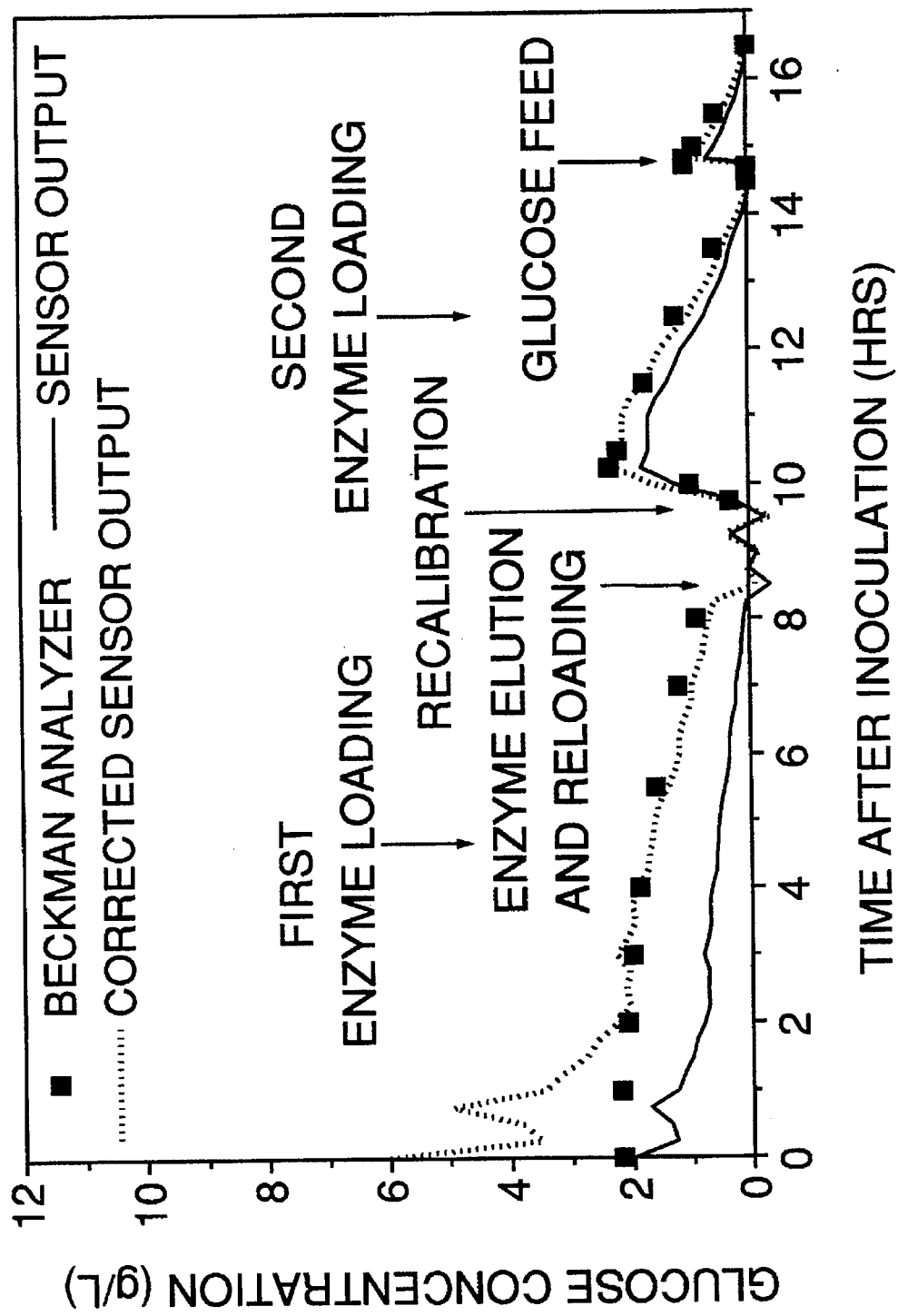
FIG. 12 is a graph showing medium glucose concentration measured by both the biosensor of the present invention and the Beckman off-line glucose analyzer during fed-batch cultivation of *E. coli* in minimal medium.

FIG. 12 shows the output from the prototype sensor and the results of the offline glucose analyses over the course of the experiment. These results demonstrate the effect of the analyte matrix on the sensor response and the importance of sensor calibration under appropriate conditions. From FIG. 12, it is obvious that the sensor output correlated more closely with the results of the off-line analyses after recalibration of the sensor in the fermenter broth with cells, compared to the initial calibration of the sensor in fresh medium without cells. After reloading the enzyme and recalibrating the sensor, the profile of the sensor output followed the profile of the off-line analyses with substantially greater fidelity than the preceding phase, correctly indicating the exhaustion of the medium glucose and accurately following the infusion of glucose (and without significant delay. The improved correlation was expected, since the inaccuracies of the off-line analyzer and the unresolved effects of the analyte matrix were included in the sensor calibration constants after recalibration. Inoculation of the fermenter following the initial calibration in fresh medium changed the composition of the sample matrix, therefore calibration of the sensor would have best been performed after inoculation and after measurement of the background (ie., prior to loading the enzyme). Ideally, on-line calibration could be performed without disturbing the fermentation by using a series of internal calibration standards in a scheme similar to that proposed by Bradley and Schmid (1992)[34]. Alternatively, the sensor could be calibrated by adding glucose to the medium in aliquots after inoculation and determining the substrate concentration after each aliquot by calculation or by using the off-line glucose analyzer (in the same manner as calibration was performed following the second enzyme loading in this experiment).

[34] Supra at 7.

The glucose concentrations determined by the prototype sensor were consistently lower than the results obtained from the off-line glucose analyzer. This behaviour may have been due to effects of the analyte matrix and/or systematic differences between the two analytical methods. These observations are consistent with similar comparisons published in the literature. An empirical model was formulated for the sensor calibration curve which was used to experiment with corrections to the sensor calibration constants in an attempt to fit the sensor output more closely to the off-line glucose analyzer results. The Michaelis-Menten function used for the conversion of the measured sensor current (μA) to glucose concentration (g/L) was obtained by the equation below. An additional parameter, $I_o$ was included to represent the value of the sensor baseline current which is normally subtracted from the measured sensor current before conversion, giving:

$$S = \frac{(I - I_o)K_m}{I_{max} - (I - I_o)}$$

where S is the glucose concentration (g/L), I is the measured sensor current (μA), $I_o$ is the sensor baseline (μA), $I_{max}$ is the maximum sensor current (μA), and $K'_m$ is the apparent Michaelis constant (g/L). Using numerical analysis and several initial values for the parameters $I_o$, $I_{max}$ and $K'_m$, the corrected sensor output shown in FIG. 12 was determined.

The corrected and uncorrected sensor calibration constants for the first and second enzyme loadings are shown in Table 3.

TABLE 3

Prototype sensor calibration constants for the first and second enzyme loadings.

| Parameter | Load #1 | | Load #2 | |
| --- | --- | --- | --- | --- |
| | Uncorrected | Corrected | Uncorrected | Corrected |
| $I_o$ (µA) | 0.014 | 0.0068 | 0.0068 | 0.0068 |
| $I_{max}$ (µA) | 0.047 | 0.040 | 0.0127 | 0.0135 |
| $K_m$ (mM) | 8.6 | 9.99 | 6.44 | 10.10 |
| Correlation Coefficient | 0.9797 | 0.9710 | 0.9856 | 0.9917 |

The results were found to be reasonable. The calibration constants for the first enzyme loading could be corrected significantly by adjusting the baseline to account for the change in the analyte matrix after inoculation. The value used for the sensor baseline was the background signal determined during the fermentation (measured by lowering the internal electrode unit into contact with the cellulose matrix after elution of the enzyme and recording the sensor current). This valve was taken to be relatively constant throughout the experiment, making the assumption that the membrane system effectively rejected interfering species and resisted fouling during the course of the fermentation. The apparent Michaelis constant was found to be nearly identical for the first and second enzyme loading, which is consistent with the results achieved for multiple cycles of enzyme loading and elution using the modified rotating disk electrode. The values of $I_{max}$ which can be taken to be representative of the amount of enzyme loaded, were not changed significantly by the correction procedure.

It can be seen from FIG. 12 that, after applying the corrected sensor calibration constants, the sensor output matches the results profile from the off-line analyses much more accurately. The transient fluctuations in the sensor output observed at the beginning of the experiment are not normally observed in the medium glucose concentration and are presumed to be a result of some initial instability in the local environment of the probe (eg., due to entrapped bubbles), although the actual cause in this case could not be determined. In any case, the perturbation temporary and did not recur. Once the perturbation subsided, the correlation between the corrected sensor output and the off-line results was excellent.

The approach used above assumes that the off-line glucose analyzer was precise and accurate and that the sensor output was in error. According to some researchers, the accuracy of the measured value of a single sensor can normally be validated by comparison with alternative measurement methods. Unfortunately, different measuring methods often will produce different results and the most accurate analytical method cannot easily be determined. This is especially true in the case of biological systems, which are frequently more difficult to measure accurately than simple physical or chemical systems. Comparison of the off-line glucose analyzer results immediately after inoculation (2.17 g/L) with the glucose sensor output (1.98 g/L), and the calculated medium glucose concentration (2.40 g/L, based on the volume of medium and the amount of glucose added) reveals a significant discrepancy in both methods. The choice of the most accurate and/or reliable analytical method must often be based on experience. In this experiment, the results from the Beckman glucose analyzer were used as the standard for comparison for reasons of practicality, availability, and relative ease of use.

To determine the useable lifetime of the enzyme component of the sensor, periodic internal calibration checks could be performed to determine at what point the activity of the enzyme had deteriorated to an unsatisfactory degree. In this experiment, the results from off-line glucose analysis of medium samples were used as a reference in an attempt to identify drift in the prototype sensor output which could be attributed to enzyme deactivation over time. This approach makes the assumption that the results from the offline glucose analyzer were stable and reliable over time. With respect to this, care was taken to recalibrate the glucose analyzer before analyzing each medium sample. It was expected that if some systematic discrepancy existed between the off-line glucose analyzer and the glucose sensor output, the error would be consistent over time unless some process of membrane or electrode fouling or enzyme deactivation modified the results from one (or both) of the sensor(s). The results overall indicate that continuous glucose monitoring could possibly be performed for at least 6 hours before elution and replacement of the enzyme would be necessary.

EXAMPLE 7

Glucose Monitoring during Fed-Batch Cultivation of E. coli

Organisms

A strain of E. coli JM101/pTUgE07K3 was used for the cultivation. The organism contained the plasmid for the production of $CBD_{Cex}$ and was stored in 10% DMSO at $-70°$ C. The plasmid consisted of the tac promoter and the leader sequence of C. fimi exoglucanase (Cex), followed by the structural gene for $CBD_{Cax}$. The resistance marker was kanamycin and the inducer was IPTG (E. Ong, unpublished results). The inducer was not added in this experiment.

Media:

Minimal medium M-9 was prepared with the following composition (g/L): $Na_2HPO_4$, 11.76; $KH_2PO_4$, 5.88; NaCl, 0.5; $NH_4Cl$, 1.0; $MgSO_4$, 0.49; $CaCl_2$, 0.01; thiamine, 1.685; kanamycin, 0.025; and the following trace metals (mg/L): $Al_2(SO_4)_3 \cdot 7H_2O$, 0.040; $CoCl_2 \cdot 6H_2O$), 0.032; $CuSO_4 \cdot 5H_2O$), 0.008; $H_3BO_3$, 0.004; $MnCl_2 \cdot 4H_2O$), 0.080; $NiCl_2 \cdot 6H_2O$), 0.004; $Na_2MoO_4 \cdot 2H_2O$), 0.020; $ZnSO_4 \cdot 7H_2O$, 0.020. The starting glucose concentration was 2.40 g/L. Medium for the inoculum was prepared as follows (g/L): $Na_2HPO_4$, 6.00; $KH_2PO_4$, 3.00; NaCl, 0.5; $NH_4Cl$, 1.0; $MgSO_4$, 0.49; $CaCl_2$, 0.01; thiamine, 3.37; kanamycin, 0.05; glucose, 2.80 g/L.

Cultivation:

The cultivation was performed in a 20 L Chemap Type SG fermenter with the standard blade stirrer and three 25 mm side-ports. The fermenter working volume was 8 L. A 500 mL inoculum was prepared in shake flask culture. One side-port was used for the Inbold InFit 764-50 pH electrode. A second side-port was used for an optical density monitor (Cerex MAX Cellmass Sensor Probe, Cerex Corporation, Ijamsville, Md. U.S.A.). The third side-port was used for the glucose biosensor prototype. A 19 mm diameter Ingold sterilizable $O_2$ probe (No. 40180-03) was inserted through a port in the fermenter head plate. For the purpose of monitoring glucose concentration with the glucose biosensor prototype, it was unnecessary to use aseptic techniques during the fermentation.

The Chemap 3000 Series base unit and controller were used. Initially, the air flow rate was set at 6 L/min and stir rate was controlled between 50 and 700 rpm in order to maintain the dissolved oxygen setpoint at 95% of the air saturation. As the fermentation reached higher cell density, it was necessary to increase the air flow rate to 7.5 L/min and decrease the dissolved oxygen setpoint to 80%. Temperature was controlled at 37° C. Medium pH was uncontrolled.

Analyses:

Samples were withdrawn from the fermenter at different intervals using the sampling/harvesting valve. Glucose concentration in each sample was analyzed using the Beckman Glucose Analyzer 2 (Beckman Instruments Inc., Fullerton, Calif., U.S.A.) after centrifuging the sample at 14,000 rpm for 2 minutes. The absorbance of each sample at 600 nm (versus distilled water) was also measured using a Varian DMS200 UV-VIS spectrophotometer (Varian Pty. Limited, Mulgrave, Victoria, Australia). In addition, the Genesis Control Series software package (Iconics, Foxborough, Mass., U.S.A.) was used to log temperature, pH, dissolved oxygen tension, stir rate, and optical density from the on-line sensor every five minutes during the course of the fermentation.

The response of the prototype could be calibrated with respect to glucose concentration up to at least 23 mM (the maximum concentration tested) in medium without cells. The sensor signal was relatively stable and noise-free, demonstrating less than 5% variation per hour and signal noise less than 1% of the sensor current. The GOx-CBD conjugate could be loaded and eluted successfully using the inlet and outlet tubing of the modified Ingold probate body and the loading and elution protocols described above. After elution of the enzyme, the sensor response to glucose was less than or equal to the baseline signal, confirming that the enzyme had indeed been eluted.

The Whatman qualitative filter paper proved to be a satisfactory cellulose matrix for the biosensor prototype. The low mass transfer resistance of the filter paper compared to the other cellulose matrices tested was advantageous in terms of fast sensor response time and low signal attenuation due to the matrix. The filter paper also had a high porosity and cellulose surface area for binding the GOx-CBD conjugate, and was anticipated to be more easily perfused with the reagent solutions than the regenerated cellulose dialysis membrane or the nitrocellulose protein transfer membrane. Structural stability of the filter paper was not a problem, as in the RDE experiments, due to the absence of shear stress from stirring or rotation.

We claim:

1. A biosensing system including a selectively permeable interface membrane which is separate and distinct from an electrode and protein receiving matrix, and which is used to separate biochemical, optical or other processes from an analyte matrix, said membrane comprising a supporting mesh and a perfluorosulfonic acid polymer impregnated substrate.

2. A biosensing system of claim 1 wherein the substrate is selected from the group consisting of cellulose, cellulose acetate, nitrocellulose, polysulfone, polyvinylchloride, polyurethane and polyvinylalcohol.

3. A biosensing system of claim 1 wherein the substrate is cellulose triacetate.

4. A method of preparing a selectively permeable interface membrane in a biosensor system which is separate and distinct from an electrode and protein-receiving matrix, and which is used to separate biochemical, optical or other processes from an analyte matrix which comprises:

fixing a substrate onto a supporting mesh to form a substrate membrane;

casting a perfluorosulfonic acid polymer on the substrate membrane; and curing the product so formed.

5. The method of claim 4 wherein the substrate is selected from the group consisting of cellulose, cellulose acetate, nitrocellulose, polysulfone, polyvinylchloride, polyurethane and polyvinylalcohol.

6. The method of claim 4 wherein the substrate is cellulose triacetate.

7. The method of claim 4 wherein the supporting mesh is a metallic screen selected from the group consisting of stainless steel, aluminum, copper, silver and gold.

8. The method of claim 4 wherein the supporting mesh is a polymeric screen selected from the group consisting of poly(vinylchloride), poly(tetrafluoroethylene), polystyrene and polycarbonate.

9. The method of claim 4 wherein the supporting mesh is a fibrous filter material.

10. A regenerable biosensor probe for positioning in an environment characterized by the presence of biological molecules which are substrates for or products produced by enzymes in order to determine the presence of said molecules, said biosensor probe comprising:

a selectively permeable interface membrane which separates the biochemical and electrochemical processes from the environment when the probe is in place;

a porous protein-receiving matrix adjacent to the interface membrane;

an indicating electrode covered with an electrically insulative material, said electrode abutting, at one of its ends, the protein-receiving matrix;

an inlet conduit through which fresh protein conjugate may flow to the protein-receiving matrix; and an outlet conduit through which spent protein conjugate may be removed from the protein-receiving matrix.

11. The biosensor probe of claim 10 wherein the protein conjugate comprises the cellulose binding domain extracted from bacteria of the genus Cellulomonas.

12. The biosensor probe of claim 10, wherein the interface membrane comprises a supporting mesh and a perfluorosulfonic acid impregnated substrate.

* * * * *